US011529069B2

(12) United States Patent
Novikov et al.

(10) Patent No.: US 11,529,069 B2
(45) Date of Patent: Dec. 20, 2022

(54) SYSTEM, METHOD AND COMPUTER-ACCESSIBLE MEDIUM FOR FACILITATING NOISE REMOVAL IN MAGNETIC RESONANCE IMAGING

(71) Applicant: New York University, New York, NY (US)

(72) Inventors: Dmitry Novikov, New York, NY (US); Gregory Lemberskiy, Brooklyn, NY (US); Steven H. Baete, Summit, NJ (US); Jelle Veraart, Essen (BE); Els Fieremans, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 17/109,050

(22) Filed: Dec. 1, 2020

(65) Prior Publication Data

US 2021/0076972 A1    Mar. 18, 2021

Related U.S. Application Data

(63) Continuation of application No. PCT/US2019/035246, filed on Jun. 3, 2019.
(Continued)

(51) Int. Cl.
*A61B 5/00* (2006.01)
*A61B 5/055* (2006.01)
(Continued)

(52) U.S. Cl.
CPC ............ *A61B 5/055* (2013.01); *A61B 5/0042* (2013.01); *G01R 33/3854* (2013.01);
(Continued)

(58) Field of Classification Search
CPC ...................................................... A61B 5/055
See application file for complete search history.

(56) References Cited

U.S. PATENT DOCUMENTS

| 7,649,353 B2 | 1/2010 | Feiweier et al. |
| 9,841,482 B2 | 12/2017 | Fuderer et al. |
| (Continued) | | |

FOREIGN PATENT DOCUMENTS

| WO | 2008/031546 | 3/2008 | |
| WO | WO-2016187148 A1 * | 11/2016 | ....... G01R 33/56341 |

OTHER PUBLICATIONS

Veraart et al. Diffusion MRI noise mapping using random matrix theory (Year: 2016).*
(Continued)

*Primary Examiner* — Joseph M Santos Rodriguez
(74) *Attorney, Agent, or Firm* — Hunton Andrews Kurth LLP

(57) ABSTRACT

An exemplary system, method and computer-accessible medium for generating a denoised magnetic resonance (MR) image(s) of a portion(s) of a patient(s) can be provided, which can include, for example, generating a plurality of MR images of the portion(s), where a number of the MR images can be based on a number of MR coils in a MR apparatus used to generate the MR images, generating MR imaging information by denoising a first one of the MR images based on another one of the MR images, and generating the denoised MR image(s) based on the MR imaging information. The number of the MR coils can be a subset of a total number of the MR coils in the MR apparatus. The number of the MR coils can be a total number of the MR coils in the MR apparatus. The MR information can be generated by denoising each of the MR images based on the other one of the MR images.

23 Claims, 20 Drawing Sheets

Related U.S. Application Data

(60) Provisional application No. 62/679,761, filed on Jun. 1, 2018.

(51) Int. Cl.
*G01R 33/385* (2006.01)
*G01R 33/48* (2006.01)
*G01R 33/563* (2006.01)

(52) U.S. Cl.
CPC ..... *G01R 33/4806* (2013.01); *G01R 33/4808* (2013.01); *G01R 33/56341* (2013.01)

(56) References Cited

U.S. PATENT DOCUMENTS

| | | |
|---|---|---|
| 2010/0013472 A1 | 1/2010 | Buehrer et al. |
| 2015/0061668 A1 | 3/2015 | Dannels |
| 2017/0307712 A1 | 10/2017 | Cai et al. |
| 2018/0120404 A1 | 5/2018 | Novikov et al. |
| 2019/0004132 A1* | 1/2019 | Tan ................ G01R 33/4818 |

OTHER PUBLICATIONS

International Search Report for International Patent Application No. PCT/US2019/035246 dated Oct. 9, 2019.
International Written Opinion for International Patent Application No. PCT/US2019/035246 dated Oct. 9, 2019.
Communication Pursuant to Rules 161(2) and 162 EPC for European Patent Application No. 19811892.9 dated Feb. 9, 2021.
T. E. Conturo et al. "Tracking neuronal fiber pathways in the living human brain," Pro---.ceedings of the National Academy of Sciences 96, 10422-10427 (1999), arXiv:NIHMS 150003.
Peter J Basser et al. "In Vivo Fiber Tractography," Magnetic Resonance in Medicine 44, 625-632 (2000).
Saad Jbabdi et al. "Measuring macroscopic brain connections in vivo," Nature Neuroscience 18, 1546-1555 (2015).
Klaus H. Maier-Hein et al. "The challenge of mapping the human connectome based on diffusion tractography," Nature Communications 8 (2017), 10.1038/s41467-017-01285-x.
S Ogawa et al. "Brain magnetic resonance imaging with contrast dependent on blood oxygenation." Proceedings of the National Academy of Sciences of the United States of America 87, 9868-9872 (1990).
J W Belliveau et al. "Functional mapping of the human visual cortex by magnetic resonance imaging." Science (New York, N.Y.) 254, 716-9 (1991).
Seiji Ogawa et al. "Intrinsic signal changes accompanying sensory stimulation: Functional brain map¬ping with magnetic resonance imaging," Proc Natl Acad Sci U S A 89, 5951-5955 (1992).
M E Moseley et al. "Early detection of regional cerebral-ischemia in cats—comparison of diffusion-weighted and T2-weighted MRI and spectroscopy," Magnetic Resonance In Medicine 14, 330-346 (1990).
P C Lauterbur, "Image formation by induced local interactions. Examples employing nuclear magnetic resonance," Nature (London, United Kingdom) 242, 190-191 (1973).
P. B. Roemer et al. "The NMR phased array," Magnetic Resonance in Medicine 16, 192-225 (1990).
Florian Wiesinger et al "Electrodynamics and ultimate SNR in parallel MR imaging," Magnetic Resonance in Medicine 52, 376-390 (2004).
Riccardo Lattanzi et al. "Ideal current patterns yielding optimal signal-to-noise ratio and specific absorption rate in magnetic resonance imaging: Computational methods and physi¬cal insights," Magnetic Resonance in Medicine 68, 286-304 (2012).
Joseph R Corea et al. "Screen-printed flexible MRI receive coils," Nature Communications 7, 10839 (2016).
HáKon Gudbjartsson et al. "The rician distribution of noisy MRI data," Magnetic Reso¬nance in Medicine 34, 910-914 (1995).

Eugene P. Wigner et al. "On the Distribution of the Roots of Certain Symmetric Matrices," Annals of Math¬ematics 67, 325-327 (1958).
Freeman J. Dyson, "A BrownianMotion Model for the Eigenvalues of a Random Matrix," Journal of Mathematical Physics 3, 1191-1198 (1962).
V A Marchenko and L A Pastur, "Distribution of Eigenvalues for Some Sets of Random Matrices," Mathematics of the USSR-Sbornik 1, 457-483 (1967).
Jinho Baik et al. "Phase transition of the largest eigenvalue for nonnull complex sample covariance matrices," The Annals of Probability 33, 1643-1697 (2005).
Iain M. Johnstone, "High dimensional statistical inference and random matrices," Proceedings of the International Congress of Mathematicians, Madrid, Aug. 22-30, 2006 , 307-333 (2007), arXiv:0611589.
Dan Ma, Vikas Gulani "Magnetic resonance fingerprinting," Nature 495, 187-192 (2013).
Kerstin Hammernik et al. "Learning a variational network for reconstruction of accelerated mri data," Magnetic Resonance in Medicine 79, 3055-3071 (2018).
Bo Zhu et al. "Image recon¬struction by domain-transform manifold learning," Nature 555, 487-492 (2018).
Ogan Ocali and Ergin Atalar, "Ultimate intrinsic signal-to-noise ratio in MRI," Magnetic Resonance in Medicine 39, 462-473 (1998).
Qiuyun Fan et al. "MGH-USC Human Connectome Project datasets with ultra-high b-value diffusion MRI," NeuroImage 124, 1108-1114 (2016).
Thomas F. Budinger et al. "Toward 20 t magnetic resonance for human brain studies: opportunities for discovery and neuroscience rationale," Magnetic Resonance Materials in Physics, Biology and Medicine 29, 617-639 (2016).
Oliver Kraff and Harald H. Quick, "7t: Physics, safety, and potential clinical applications," Journal of Magnetic Resonance Imaging 46, 1573-1589 (2017), https://onlinelibrary.wiley.com/doi/pdf/10.1002/jmri.25723.
Allahyar Kangarlu and Pierre-Marie L Robitaille, "Biological effects and health implications in mag¬netic resonance imaging," Concepts in Magnetic Resonance: An Educational Journal 12, 321-359 (2000).
C. W. J. Beenakker, "Random-matrix theory of quantum transport," Rev. Mod. Phys. 69, 731-808 (1997).
Jelle Veraart et al. "Denoising of diffusion MRI using random matrix theory," NeuroImage 142, 394-406 (2016).
Jelle Veraart et al. "Diffusion MRI noise mapping using random matrix theory," Magnetic resonance in medicine 76, 1582-1593 (2016).
M. Gavish and D. L. Donoho, "Optimal shrinkage of singular values," IEEE Transactions on Informa¬tion Theory 63, 2137-2152 (2017).
David O. Walsh, Arthur F. Gmitro, and Michael W. Marcellin, "Adaptive reconstruction of phased array MR imagery," Magnetic Resonance in Medicine 43, 682-690 (2000).
D S Novikov et al. "Quantifying brain microstructure with diffusion MRI: Theory and parameter estimation," NMR in Biomedicine 32, e3998 (2019).
C B Ahn and Zang Cho, "A new phase correction method in nmr imaging based on autocorrelation and histogram analysis," IEEE transactions on medical imaging 6, 32-6 (1987).
Victor B Xie et al. "Robust epi nyquist ghost removal by incorporating phase error correction with sensitivity encoding (pec-sense)," Magnetic resonance in medicine 79 (2017), 10.1002/mrm.26710.
Benjamin Ades-Aron et al. "Evaluation of the accuracy and precision of the diffusion parameter estimation with gibbs and noise removal pipeline," NeuroImage 183, 532-543 (2018).
Klaas P Pruessmann, "Encoding and reconstruction in parallel MRI," NMR in Biomedicine 19, 288-299 (2006).
Mark A. Griswold et al. "Generalized Autocalibrating Partially Parallel Acquisitions (GRAPPA)," Magnetic Resonance in Medicine 47, 1202-1210 (2002).
Martin Uecker et al. "Espiritâan eigenvalue approach to autocalibrating parallel mri: where sense meets grappa," Magnetic resonance in

(56) References Cited

OTHER PUBLICATIONS medicine : official journal of the Soci¬ety of Magnetic Resonance in Medicine / Society of Magnetic Resonance in Medicine 71 (2014), 10.1002/mrm.24751.

Cornelius Eichner et al. "Real diffusion-weighted mri enabling true signal averaging and in¬creased diffusion contrast," NeuroImage 122 (2015).

Tim Sprenger et al. "Real valued diffusion-weighted imaging using decorrelated phase filtering," Magnetic Resonance in Medicine 77, n/a-n/a (2016).

Matt A. Bernstein et al. "Chapter 16—echo train pulse sequences," in Handbook of MRI Pulse Sequences (Academic Press, Burlington, 2004) pp. 702-801.

N. Martini et al. "Noise correlations and snr in phased-array mrs," NMR in Biomedicine 23, 66-73 (2010), https://onlinelibrary.wiley.com/doi/pdf/10.1002/nbm.1429.

Katherine L. Wright et al. "Non-cartesian parallel imaging reconstruction," Journal of Magnetic Resonance Imaging 40, 1022-1040 (2014), https://onlinelibrary.wiley.com/doi/pdf/10.1002/jmri.24521.

G. McGibney et al. "Quantitative evaluation of several partial fourier reconstruction algorithms used in mri," Magnetic Resonance in Medicine 30, 51-59 (1993), https://onlinelibrary.wiley.com/doi/pdf/10.1002/mrm.1910300109.

Paul Margosian et al. "Faster mr imaging: Imaging with half the data," SPIE vol. 593, Medical Imaging Processing (1985).

Laurent Laloux et al. "Noise Dressing of Finan¬cial Correlation Matrices," Physical Review Letters 83, 1467-1470 (1999), vv:9810255 [cond-mat].

S Jbabdi et al. "A Bayesian framework for global tractography," NeuroImage 37, 116-129 (2007).

Cheng Guan Koay et al. "A signal transformational framework for breaking the noise floor and its applications in MRI," Journal of Magnetic Resonance 197, 108-119 (2009).

Emilie T McKinnon et al. "Dependence on b-value of the direction-averaged diffusion-weighted imaging signal in brain," Magnetic Resonance Imaging 36, 121-127 (2016).

Jelle Veraart et al. "NeuroImage on the scaling behavior of water diffusion in human brain white matter," NeuroImage 185, 379-387 (2019).

S Mori, B J Crain, V P Chacko, and P C van Zijl, "Three-dimensional tracking of axonal projections in the brain by magnetic resonance imaging." Ann Neurol 45, 265-269 (1999).

Derek K Jones, Diffusion MRI: Theory, Methods, and Applications (Oxford University Press, New York, 2010).

Matt A. Bernstein, Kevin F. King, and Xiaohong Joe Zhou, "Chapter 16—echo train pulse sequences," in Handbook of MRI Pulse Sequences, edited by Matt A. Bernstein, Kevin F. King, and Xiaohong Joe Zhou (Academic Press, Burlington, 2004) pp. 702-801.

European Search Report dated Feb. 17, 2022 for European Patent Application No. 19811892.9.

G. Lemberskiy et al. "Achieving sub-mm clinical diffusion MRI resolution by removing noises during reconstruction using random matrix theory," International Society for Magnetic Resonance in Medicine, No. 770, Apr. 26, 2019.

\* cited by examiner

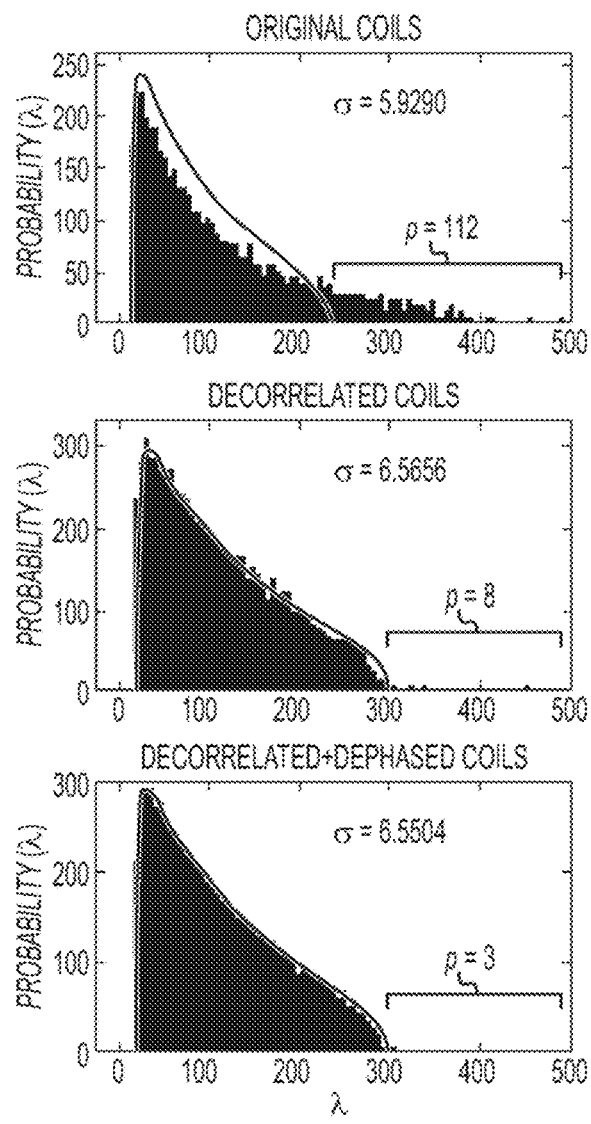
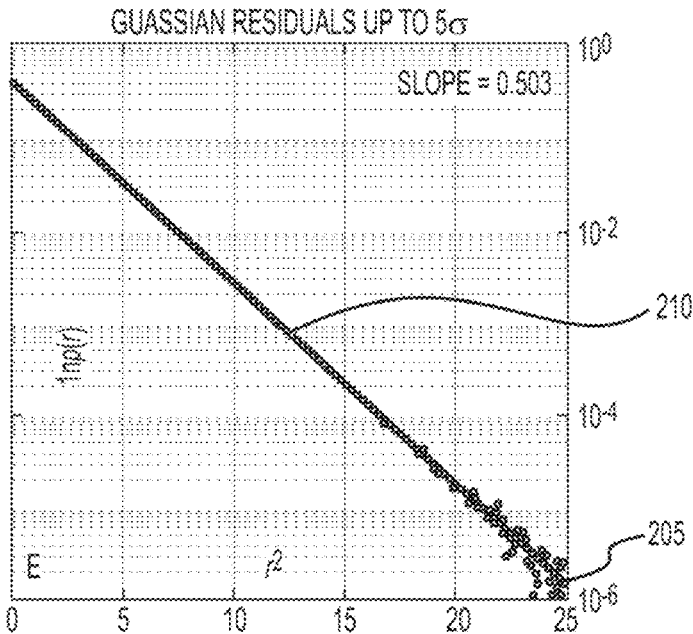
FIG. 2D

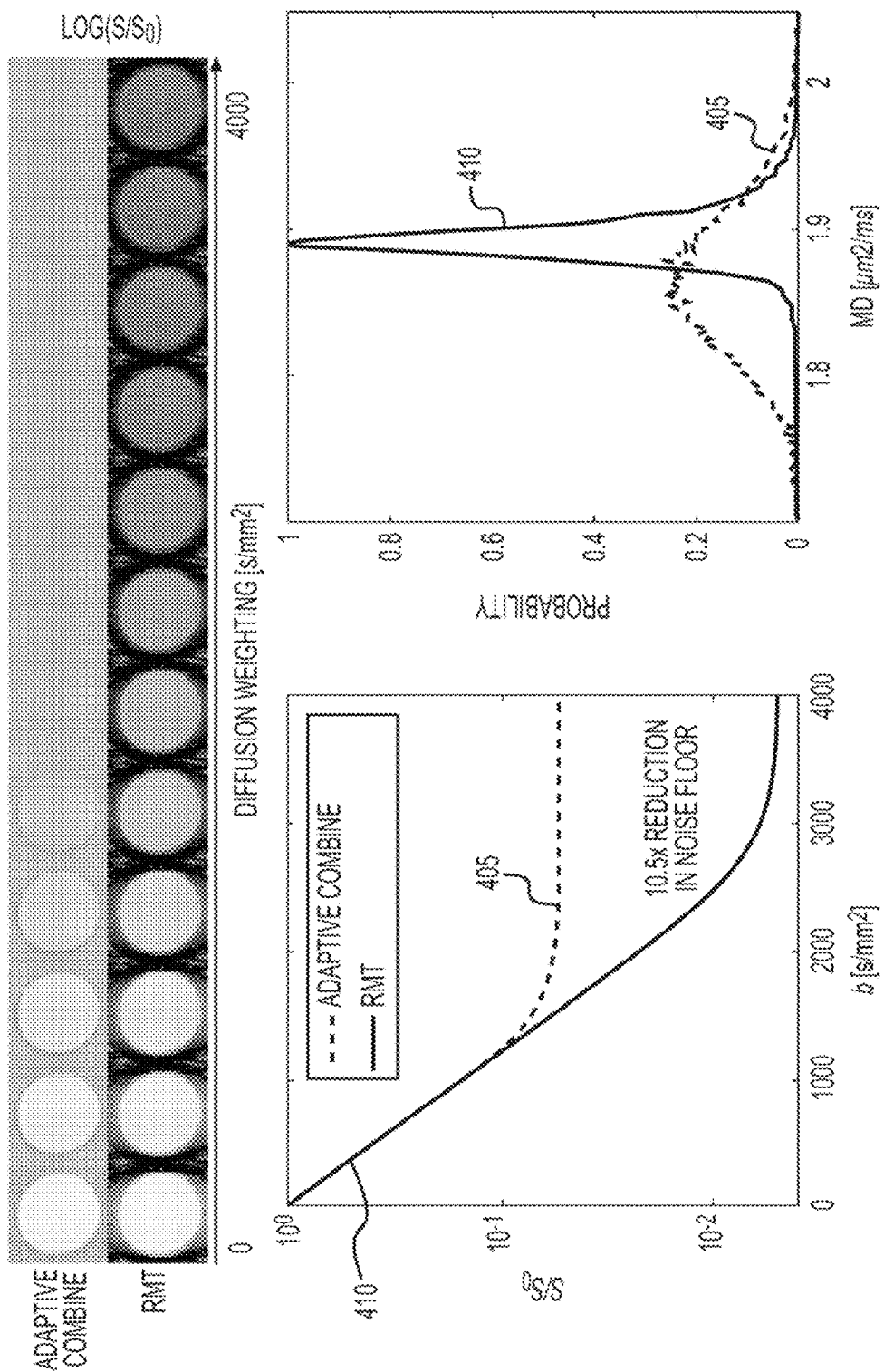

SYSTEM, METHOD AND COMPUTER-ACCESSIBLE MEDIUM FOR FACILITATING NOISE REMOVAL IN MAGNETIC RESONANCE IMAGING

CROSS-REFERENCE TO RELATED APPLICATION(S)

This application is a continuation of, relates to, and claims the benefit and priority from International Patent Application No. PCT/US2019/035246 filed on Jun. 3, 2019 that published as International Patent Publication No. WO 2019/232539 on Dec. 5, 2019, which claims the benefit and priority from U.S. Provisional Patent Application Ser. No. 62/679,761, filed on Jun. 1, 2018, the entire disclosures of which are incorporated herein by reference.

FIELD OF THE DISCLOSURE

The present disclosure relates generally to magnetic resonance imaging ("MRI"), and more specifically, to exemplary embodiments of exemplary systems, methods and computer-accessible medium for facilitating noise removal in magnetic resonance imaging.

BACKGROUND INFORMATION

MRI is a super-resolution imaging technique. Contrary to optical and X-ray imaging, the spatial resolution of MRI is not limited by the radio frequency (RF) wavelength. Instead, the resolution of MRI is limited by the signal-to-noise ratio ("SNR") (see, e.g., References 11-14), which is proportional to the imaging voxel volume for a given field strength and coil/body geometry. A reduction of a voxel by twofold in each dimension likely requires a $2^3=8$-fold SNR increase. Unfortunately, SNR increase by designing better MRI receivers (e.g., RF coils or coil arrays) has already achieved near-optimal SNR efficiency, approaching 90% of the Ultimate Intrinsic SNR (see, e.g., Reference 24), as observed experimentally (see, e.g., Reference 25), and validated in simulations. (See, e.g., Reference 13, 26). The signal can also be enhanced by imaging at greater field strength. (See, e.g., Reference 27). Cost and engineering constraints (see, e.g., Reference 28), such as magnetic field inhomogeneity and bore size, as well as physiological constraints (see, e.g., References 29 and 30), such as nerve stimulation, nausea and nystagmus, make this route challenging, with the clinical MRI scanners dominated by 1.5-3 T magnets.

Alternatively, SNR can be increased by reducing the noise for a given hardware setup. The most direct way to lower the noise level is by averaging images together. This is costly, however, as SNR grows slowly, as a square root of the number of averages, for example, doubling spatial resolution would likely require a clinically prohibitive $8^2=64$-fold scan time increase. Longer scans further complicate the measurement through motion and physiological artifacts (e.g., cardiac and respiratory motion).

Thus, it may be beneficial to provide an exemplary system, method and computer-accessible medium for noise reduction in magnetic resonance imaging, which can overcome at least some of the deficiencies described herein above.

SUMMARY OF EXEMPLARY EMBODIMENTS

An exemplary system, method and computer-accessible medium for generating a denoised magnetic resonance (MR) image(s) of a portion(s) of a patient(s) can be provided, which can include, for example, generating a plurality of MR images of the portion(s), where a number of the MR images can be based on a number of MR coils in a MR apparatus used to generate the MR images, generating MR imaging information by denoising a first one of the MR images based on another one of the MR images, and generating the denoised MR image(s) based on the MR imaging information. The number of the MR coils can be a subset of a total number of the MR coils in the MR apparatus. The number of the MR coils can be a total number of the MR coils in the MR apparatus. The MR information can be generated by denoising each of the MR images based on the other one of the MR images.

In certain exemplary embodiments of the present disclosure, the MR information can be generated by denoising each of the MR images based on every one of the MR images. The number of the MR images can be further based on a real part of a signal and an imaginary part of a signal produced using the MR coils. The MR imaging information can be generated using a reconstruction procedure. The reconstruction procedure can be denoising procedure. The denoising procedure can be a random matrix theory procedure. The denoised MR image(s) can be generated using a reconstruction procedure. The reconstruction procedure can be an adaptive-combine reconstruction procedure. The number of the MRI images can be based on a MR imaging procedure being performed using the MR apparatus.

In some exemplary embodiments of the present disclosure, The MR imaging procedure(s) can be (i) diffusion imaging procedure, (ii) perfusion MR imaging, (iii) functional MR imaging, (iv) MR imaging fingerprinting, (iv) a multi-contrast imaging procedure, or (v) a multi-modal imaging procedure. The MR imaging information can be generated by decorrelating noise using a plurality of MR coil combinations. The MR imaging information can be generated using a Nyquist ghost correction procedure. The Nyquist ghost correction procedure can be based on odd scan lines and even scan lines. The MR imaging information can be generated based on an estimated coil sensitivity for each of the MR coils. The MR imaging information can be generated using a phase estimation procedure, which can include using a principal component from a matrix with a sliding window. The MR imaging information can be generated using a phase unwinding procedure, where the phase unwinding procedure can include a joint redundancy in a phase and a measurement over all the MR coils.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIG. 2D is a set of exemplary graphs associated with the exemplary images shows in FIGS. 2A-2C according to an exemplary embodiment of the present disclosure;

FIG. 4A is a set of exemplary diffusion-weighted images for adaptive combine and radial matrix theory according to an exemplary embodiment of the present disclosure;

FIG. 4B is an exemplary graph illustrating a monoexponential straight line that can be indicative of a Gaussian diffusion in water according to an exemplary embodiment of the present disclosure;

FIG. 4C is an exemplary histogram of a mean diffusivity according to an exemplary embodiment of the present disclosure;

Figure 1B:
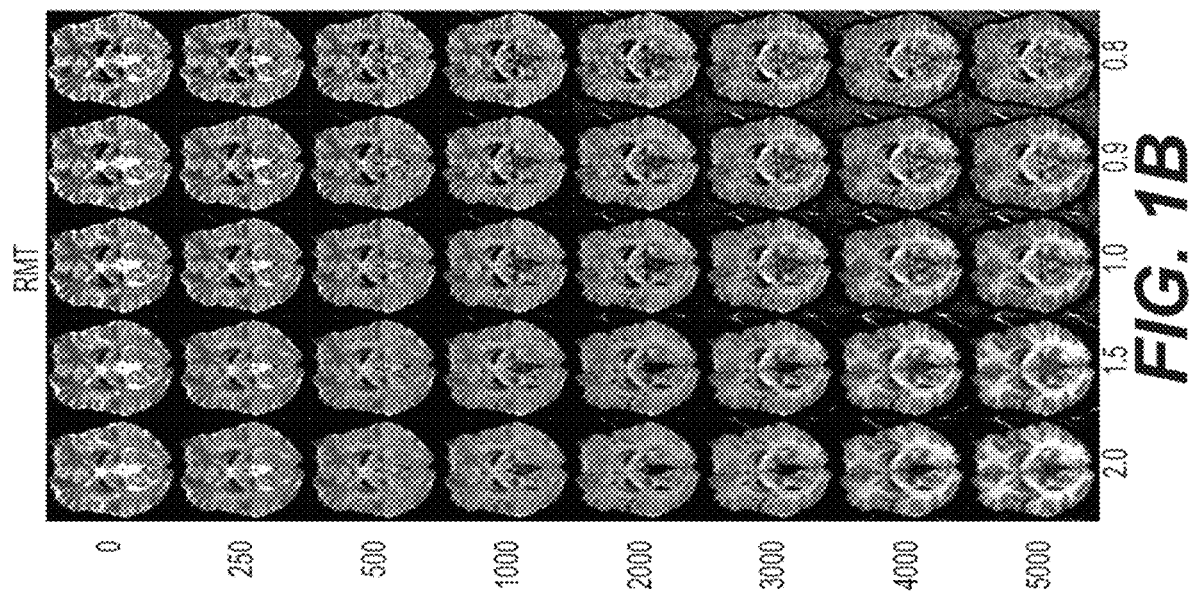
FIG. 1B is a set of exemplary images of the reconstruction of the same raw data used to generate FIG. 1A according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

The exemplary systems, methods and computer-accessible medium, according to an exemplary embodiment of the present disclosure, can be used to reduce the noise, and thus recover the MRI signal, by utilizing the redundancy in measuring the properties of the same object (e.g., a human body) from multiple vantage points, such as RF coils, MRI contrasts and specially selected patches of voxels. The exemplary systems, methods and computer-accessible medium, according to an exemplary embodiment of the present disclosure, can be used on diffusion MRI ("dMRI"), which is based on micrometer level restrictions to water diffusion, and can be a source of multiple inequivalent contrasts in the q-space of directions and diffusion weightings. (See, e.g., Reference 31). The exemplary systems, methods and computer-accessible medium, according to an exemplary embodiment of the present disclosure, can be also used on perfusion MRI, functional MRI, MRI fingerprinting, and any other multi-contrast and/or multi-modal MRI exam, and the combination of such contrasts. The more contrasts that can be used combined, the better the performance of the exemplary system, method and computer-accessible medium can be.

The use of multiple complementary contrasts can be a hallmark of MRI exams. So far, MR image reconstruction from multiple RF coils, has been performed for each image separately since the 1980s. This has been state-of-the art. The exemplary system, method and computer-accessible medium, according to an exemplary embodiment of the present disclosure, can be used for MR image reconstruction, that can utilize a combination of all images together, including but not limited to, the measurements from all RF coils from all acquired MR contrasts, which can include recognizing and removing random thermal noise from all of them at once. The quality of this noise removal can be validated by confirming a perfectly white-noise statistics of image residuals (See e.g., FIG. 2D); by quantifying biases in measuring diffusion-tensor and higher-order diffusion metrics in the human brain (See e.g., FIGS. 3A-3D) and Table I below; and on a water phantom, (See e.g., FIGS. 4A-4C), where noise is shown to be reduced by 10-fold. The exemplary system, method and computer-accessible medium, according to an exemplary embodiment of the present disclosure, can be applied to a number of clinically relevant MRI acquisitions enabling unprecedented spatial resolutions and contrasts in routine settings. (See e.g., images shown in FIGS. 5A-5D).

The exemplary analytical tool utilized to perform averaging over the noise in inequivalent measurements can be random matrix theory ("RMT") denoising or reconstruction. RMT can be used to establish universal statistical properties for ensembles of large matrices with random entries. (See, e.g., References 16 and 17). RMT was applied to explain the excitation spectra of heavy nuclei. While each entry in such a complicated Hamiltonian can be considered purely random, the distribution of its energy levels $\epsilon$ can become deterministic (e.g., Wigner's semicircle, $f_N^W(\epsilon) = \sqrt{2N - \epsilon^2}/\pi N$) in the limit of a large N×N matrix). (See, e.g., Reference 16). Such universal properties were identified in the quantum dot level statistics and mesoscopic transport (see, e.g., Reference 32), and in other fields. (See, e.g., Reference 20). To apply the concepts of RMT to an MRI measurement, and to develop a working methodology enabling SNR increase based on the RMT principles, a suitably large redundant measurement matrix X can be constructed whose statistical properties in the pure-noise case can be known, so that the noise can be recognized and removed.

As previously discussed, MRI measures signals from many receiver elements (e.g., RF coils), imaging voxels, and a multitude of MR contrasts such as echo times, q-space points or trajectories in diffusion MRI ("dMRI"), time series in perfusion or functional MRI, etc. Thus, an MR exam can be a multi-dimensional, at least 3-dimensional measurement matrix $\chi_{xcr}$ (a rank-3 tensor, or a 3-dimensional tensor), whose indices $x=1 \ldots N_x$, $c=1 \ldots N_c$ and $r=1 \ldots N_r$ correspond to voxels, contrasts and RF receive coils. Due to strong correlations between different measurements, the matrix $\chi_{xcr}$ can be expected to have much fewer independent entries than the number $N_x N_c N_r$ of its elements, while the noise can obscure its low-rank structure.

Further, MRI exams from patient-to-patient can be highly redundant, for example, most brain MRI exams look very similar due to commonly shared anatomical features. Thus, the exemplary system, method and computer-accessible medium can incorporate another dimension to an MRI measurement matrix (e.g., the fourth dimension) that can include a set of previously acquired MRI exams on this subject or on a number of other subjects (e.g., the $4^{th}$ index, s, numbering the subjects). Therefore, the overall rank of the exam matrix $\chi_{xcrs}$ (when, for example, reshaped into a 2-dimensional matrix) can be much smaller than the total number of its elements due to strong correlations between its entries. The exemplary RMT denoising procedure can be applied over numerous exams, where the precision and degree of noise-removal can improve with each patient Since the noise plays a role in the exemplary analysis, a pure-noise measurement, with all the entries of $\chi_{xcr}$ drawn from a Gaussian (e.g., white) noise with variance $\sigma^2$ can be considered. Reshaping $\chi_{xcr}$ into a rank-2 M×N signal matrix X with $MN=N_x N_c N_r$ can map it to a Wishart ensemble of random covariance matrices. (See, e.g., Reference 20). A principal components analysis ("PCA") eigenspectrum of XX'/N (where X' symbolizes matrix Hermitian conjugation) can become deterministic in the limit M, N>>1 and finite ratio $\gamma=M/N<1$, being asymptotically distributed according to the Marchenko-Pastur law (see, e.g., Reference 18), $$f^{MP}(\lambda) = \frac{\sqrt{(\lambda_+ - \lambda)(\lambda - \lambda_-)}}{2\pi\gamma\sigma^2\lambda}, \lambda_- < \lambda < \lambda_+, \quad (1)$$

where the "quarter-circle"-shaped distribution, Eq. (1), can be contained between $\lambda_\pm = \sigma^2(1\pm\sqrt{\gamma})^2$—representing the Wigner's semicircle shifted (e.g., due to positive-definite X) and divided by $\lambda$, $f^{MP}(\lambda) = f_{2\gamma\sigma^4}^W(\lambda - (1+\gamma)\sigma^2)/\lambda$. In the case of a redundant measurement with P significant components, P<<M, N, the spectrum of XX'/N can include a few spikes above the right edge $\lambda_+$ of the distribution in Eq. (1), which can carry information distinct from the noise; the emergence of spikes from the bulk MP "sea" of eigenvalues can be based on sharp thresholds on $\sigma$, similar to a phase transition in the thermodynamic limit of large M, N. (See, e.g., Reference 19). The pure-noise eigenvalues, forming the asymptotic distribution (e.g., Eq. (1)), can thus be recognized and removed by identifying them as belonging to the distribution of Eq. (1) (using, e.g., a fast $O(N)$ procedure of Reference 33), which can also yield the noise variance $\sigma^2 \equiv \int d\lambda f^{MP}(\lambda)$ as an area under the pure-noise components (see, e.g., Reference 34), thus facilitating an objective threshold and noise estimation in the PCA denoising. Further precision improvement can be reached by undoing the eigenvalue repulsion (see, e.g., Reference 17), of the significant components from the MP bulk, by the eigenvalue shrinkage and soft thresholding of the contributions of the components around the right edge of the pure-noise distribution. (See, e.g., Reference 35).

Prior approaches in MRI have been applied after performing the image reconstruction from multiple RF coils, with the resulting rank-2 $N_x \times N_c$ measurement $X_{xc}$ given by different MR contrasts within a patch of voxels. This can be suboptimal: RF coils (e.g., typically, about 10-60 in an array) provide a way to radically increase the redundancy, not utilized within such implementations; besides, at low SNR, the magnitude MR images returned by standard reconstruction procedures (for example, adaptive combine, or "AC") can be heavily biased by the non-central-$\chi$ noise floor (see, e.g., Reference 15), with the information "squashed" and non-recoverable even after many averagings, as shown FIG. 1A. As a variant of the method, an MP-distribution-based approach can be applied to the complex data combined from RF-coils, just before taking the absolute value. As shown in FIGS. 6A-11E, parallel imaging and partial Fourier acquisitions can change the noise statistics such that MP distribution may be impossible to identify in such implementation of RMT denoising; the exact details of all the reconstruction steps can be used to calculate how they affect the noise statistics and deform the pure-noise distribution. Finally, for the RMT methodology to work for the 2-dimensional (rank-2-tensor) approach, it needs to utilize sufficiently large number $N_c$ of independent contrasts, and thereby it can fail for short protocols, as shown for a fast diffusion scan in FIG. 5A. This is why considering the denoising of 2-dimensional measurement matrices (obtained after RF coil combination for each contrast) is deemed suboptimal in the view of the present disclosure.

The exemplary system, method and computer-accessible medium, according to an exemplary embodiment of the present disclosure, can incorporate the dimension-3 or higher (e.g., rank 3 or higher tensor) measurement, including, but not limited to, the data from RF coils, contrasts, and sets of imaging voxels (or sets of MRI k-space points), and possibly, data from other subjects. The exemplary systems, methods and computer-accessible medium can utilize the following exemplary relation between the fully-sampled complex-valued signal $y_{xc}$ for a given voxel x and contrast c, and the complex-valued noise $\in_{xcr}$, written for the 3-dimensional measurement $$\chi_{xcr} = S_r(x) \cdot y_{xc} + \in_{xcr}; \langle \in_{xcr} \varepsilon^*_{x'c'r'} \rangle = \delta_{xx'} \delta_{cc'} \Psi_{rr'} \quad (2)$$

where the coil sensitivities $S_r(x) \approx S_r$ can be approximated as constant across the chosen patch of voxels, such as, but not limited to being local patch of voxels that is smaller than RF wavelength, and $\Psi_{rr'}$ can be the noise covariance matrix (e.g., estimated separately by measuring coil noise without MR excitation). (See, e.g., Reference 11). The noise covariance matrix may not be proportional to an identity matrix, and can have off-diagonal elements corresponding to coil sensitivity overlap. Thus, the noise statistics of Eq. (2) can correspond to the MP theory only after noise decorrelation, as described in the Exemplary Methods section, and demonstrated in FIGS. 2A-2D.

The relation in Eq. (2) can correspond to the following exemplary population covariance matrix:

$$\frac{1}{N_x} \sum_{x=1}^{N_x} \langle X_{xcr} X^*_{xc'r'} \rangle = S_r S^*_{r'} \frac{1}{N_x} \sum_{x=1}^{N_x} y_{xc} y^*_{xc'} + \delta_{cc'} \Psi_{rr'}, \quad (3)$$

where X can be averaged over the patch of voxels x (e.g., assuming a large enough patch, so that $N_x > N_c$, $N_r$), and $\langle \ldots \rangle$ stands for averaging over infinitely-many noise realizations. In an exemplary experiment, the noisy sample covariance matrix $$X_{\alpha\alpha'} = \frac{1}{N_x} \sum_{x=1}^{N_x} X_{xcr} X^*_{xc'r'}$$

can be measured, whose spectrum can follow the MP law in Eq. (1), after the noise decorrelation as described herein (in the Exemplary Methods section). Here, the double index $\alpha=(c, r)$, $\alpha=1 \ldots N_cN_r$ can label both contrasts and RF coils. Adding the coils can results in a large covariance matrix dimension $N=N_cN_r \sim 1000$ which can introduce extra PCA redundancy, and facilitate a sharp separation between the signal and the noise in the PCA eigenspectrum, thereby enabling high precision of noise removal in the current embodiment of the present disclosure. Thus, large N can provide an untapped reserve for a far better precision, scaling as an overall $1/\min(N, M)$, of separating noise from the signal, and of estimating relevant joint significant eigenstates and of the coil sensitivities $S_r(x)$, instead of estimating the coil sensitivities $S_r$ in separate reconstructions. The MP distribution can be formed by a much larger number N-P of pure-noise components, since $N \gg N_c$, while the number P of significant components, determined by the tissue properties, may not change. The nonzero components of the first term of Eq. (3) can be tensor products of a single $S_r$, and of P eigenvalues of the matrix $$Y_{cc'} = \frac{1}{N_x} \sum_{x=1}^{N_x} y_{xc} y^*_{xc'},$$

the same for all coils. As a variant of the current embodiment of the present disclosure, the object $\chi_{xcr}\chi^*_{xc'r'}$ derived from the 3-dimensional measurement can be traced over, for example, the "contrast" index c in the case, but not limited to, when the dimension $N_c$ can be the largest of the three (e.g., as shown in FIGS. 1-5), except the small-$N_c$ example shown in FIG. 5A, where the trace was performed over the patch of $N_x$ voxels. There can be other suitable procedures for combining the 3- or more-dimensional MRI measurement $\chi_{xcr \ldots}$ into a 2-dimensional matrix whose statistical properties can be examined to identify and remove the pure-noise contribution.

Starting from the raw coil data, for example, the exemplary rank-3 (e.g., 3-dimensional-tensor) measurement matrix $\chi_{xcr}$, can facilitate an efficiently selection to reduce it to the two-dimensional covariance matrix whose pure-noise distribution can follow Eq. (1). In order to obtain the exemplary covariance matrix $X_{\alpha\alpha'}$ from $\chi_{xcr}$, the exemplary system, method and computer-accessible medium can trace over the largest dimension of the three, with the other two representing the double index $\alpha$ as described above. The above considerations do not limit the optimal way of forming the exemplary covariance matrix $X_{\alpha\alpha'}$ employed in the RMT denoising. Additionally, there can be other suitable optimal procedures for forming $X_{\alpha\alpha'}$, all based on a rank-3 tensor object $\chi_{xcr}$. Alternatively, the generalized eigenspectrum of the object $\chi_{xcr}$ can be suitably reshaped into a rank-2 matrix $\chi$ (e.g., belonging to the Ginibre matrix ensemble), while also not reducing it to the covariance matrix. The eigenvalues of such a rank-2 matrix $\chi$ can be compared to those of the case of pure-noise measurement (e.g., those for the Ginibre matrices confined to a circle within a complex plane). Thus, the exemplary system, method and computer-accessible medium, can utilize the raw data across multiple contrasts, RF coils, and measurement voxels, or the measured points in the MRI k-space, and to separate the noise from the signal by comparing the statistics of the measured rank-3 (or higher-rank) tensor object $\chi_{xcr} \ldots$ with that of a pure-noise $\chi_{xcr} \ldots$.

One exemplary procedure to identify the pure-noise distribution (e.g. MP distribution of Eq. (1)) is to fit Eq. (1) to a spectrum of the covariance matrix $X_{aa'}$ defined above. This method is illustrated in FIGS. 2A-2D, where the MP distribution emerges after coil decorrelation. Other suitable procedures based on similarity in the space of distributions can be used to identify the pure-noise components of the MRI measurement, starting from the rank-3 tensor object $\chi_{xcr}$, such as soft thresholding/shrinkage of the eigenvalues close to the edge of the pure-noise distribution.

The exemplary system, method and computer-accessible medium, according to an exemplary embodiment of the present disclosure, can generate synthetic MRI data with the noise statistics and artifacts mimicking that of an experiment. For example, exemplary images of a human brain can be distorted with Nyquist-Johnson noise, motion, distortion, and under-sampling artifacts, to closely mimic biological tissue properties and noise statistics, to augment the measurement matrix such that RMT denoising can be applied to a larger matrix to improve the precision of identifying pure-noise components and the accuracy of their removal, and thus to enhance image quality of the acquired data.

An exemplary application of locally low rank methods of identification of noise in MR images may not be optimal. Thus, the exemplary system, method and computer-accessible medium can optimally prepare the multi-dimensional MRI data for the denoising procedure, that in turn can be, for example, based on thresholding (e.g., hard or soft) of the principal components. Below is a description of the effects of undersampling (e.g., partial Fourier or regular) and phase fluctuations due to motion and cardiac pulsation on the noise statistics, and the procedures to transform the data to a suitable form to ensure the applicability of such noise-reduction procedure(s) (e.g., noise decorrelation and phase unwinding), and to ensure that the number P of significant components does not grow too much due to different MRI-specific artifacts, ensuring enough redundancy to provide the denoising benefit.

Figure 1A:
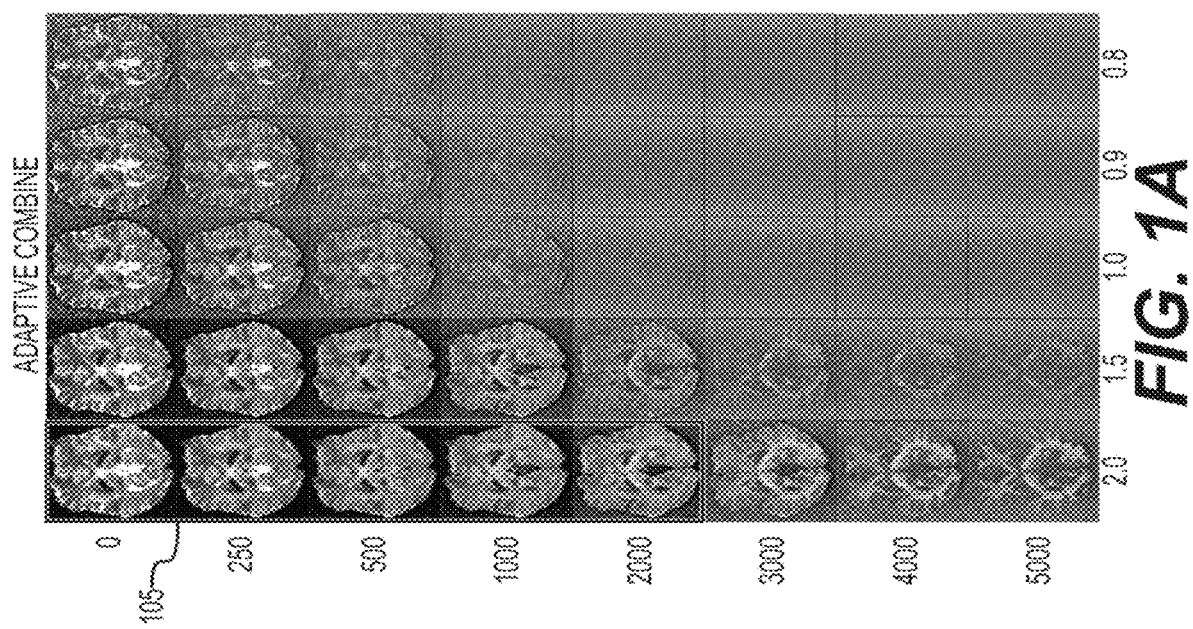
FIG. 1A is a set of exemplary images illustrating clinical diffusion MRI according to an exemplary embodiment of the present disclosure.

FIG. 1A shows a set of exemplary images illustrating clinical diffusion MRI according to an exemplary embodiment of the present disclosure. For example, current state-of-the-art clinical diffusion MRI is typically limited to voxels ≥2 mm and diffusion weightings b≤2000 s/mm² (see e.g., box 105), with higher resolutions and/or stronger weightings resulting in the prohibitive SNR decrease. dMRI was reconstructed with a standard adaptive-combine procedure, which is shown across five resolutions (e.g., [2.0, 1.5, 1.0, 0.9, 0.8] mm isotropic voxels, left-right), and eight b-values (b=0-5000 s/mm², top to bottom), directionally-averaged over each b-shell. The image quality of the currently-used dMRI greatly deteriorates with decreasing voxel size and/or diffusion weighting increase.

Figure 1C:
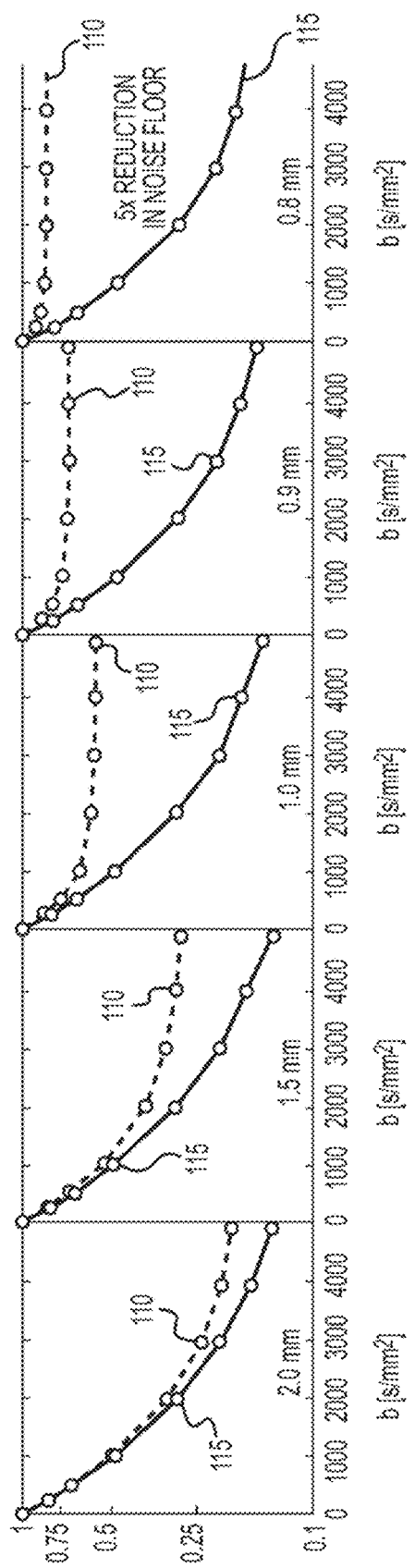
FIG. 1C is a set of exemplary graphs illustrating normalized direction-averaged dMRI signals according to an exemplary embodiment of the present disclosure.

FIG. 1B shows a set of exemplary images of the reconstruction of the same raw data used to generate FIG. 1A according to an exemplary embodiment of the present disclosure. Reconstruction of the same raw data after an exemplary embodiment of random matrix theory ("RMT") denoising (e.g., RMT reconstruction) can significantly increase the range of resolutions and diffusion weightings. FIG. 1C shows a set of exemplary graphs illustrating normalized direction-averaged dMRI signals according to an exemplary embodiment of the present disclosure. Exemplary normalized direction-averaged dMRI signals from all white matter voxels are plotted as function of the diffusion weighting b, showing an expected "squashing" of the signal by the relatively increasing Rician noise floor for the standard reconstruction (e.g., line 110), and practically unchanged noise floor for the exemplary embodiment of an RMT reconstruction (e.g., line 115), yielding at least five-fold SNR gain.

Utilizing the redundancy in multiple MM images can be almost as effective in its noise-reduction ability as taking an average over numerous measurements, even though each of them can carry somewhat different information about the object, yet can be corrupted by its own noise realization, as shown in FIGS. 2A-2D.

Figure 2A:
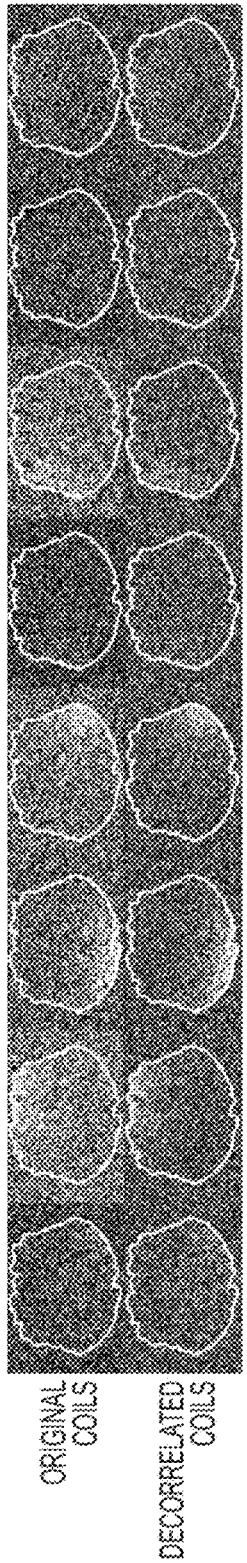
FIG. 2A is a set of exemplary images illustrating a coil noise decorrelation according to an exemplary embodiment of the present disclosure.

Magnitudes from eight coils (out of total $N_r$=16) are shown for 1 mm isotropic brain voxels (e.g., based on data shown in FIGS. 1A-1C) during main RMT reconstruction steps. FIG. 2A illustrates a set of exemplary images illustrating coil noise decorrelation according to an exemplary embodiment of the present disclosure. Coil decorrelation can be used to maintain Gaussian noise, for the MP distribution to emerge. Due to coil noise correlations, the eigenvalues do not follow MP distribution (see, e.g., Eq. (1) below), for the original coils, whereas a well-pronounced distribution (see, e.g., Eq. (1)), can appear after the decorrelation procedure, in the decorrelated-coil basis, with P~1.

Figure 2B:
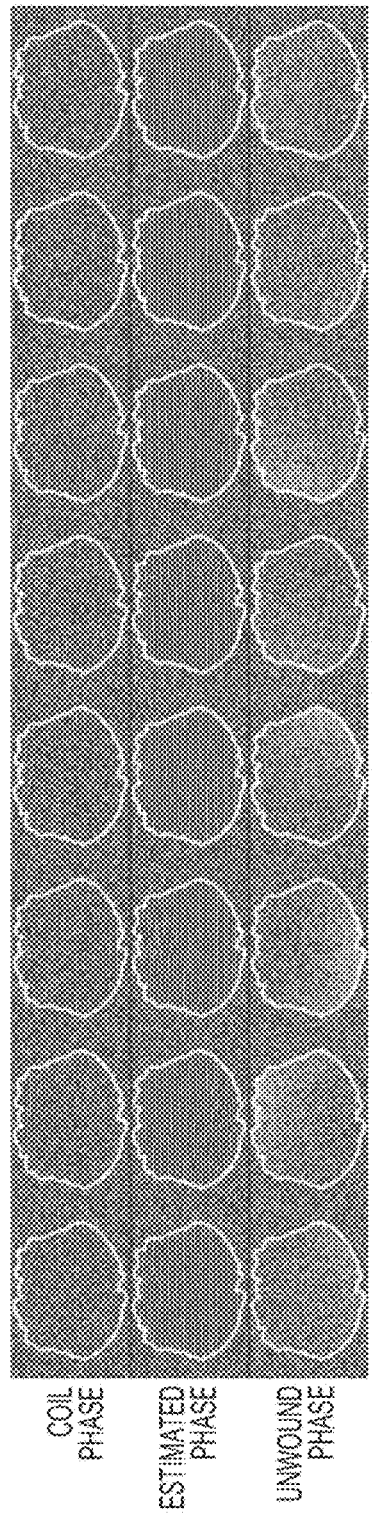
FIG. 2B is a set of exemplary images illustrating a phase removal according to an exemplary embodiment of the present disclosure.

FIG. 2B shows a set of exemplary images illustrating the phase removal according to an exemplary embodiment of the present disclosure. Further reduction of the number of significant components P can be attained by unwinding spatial phase variation across the coil images due to coil-sensitivities, motion, and under-sampling patterns. In this example, phase unwinding can facilitate a further SNR boost by $\sqrt{8/3}$.

Figure 2C:
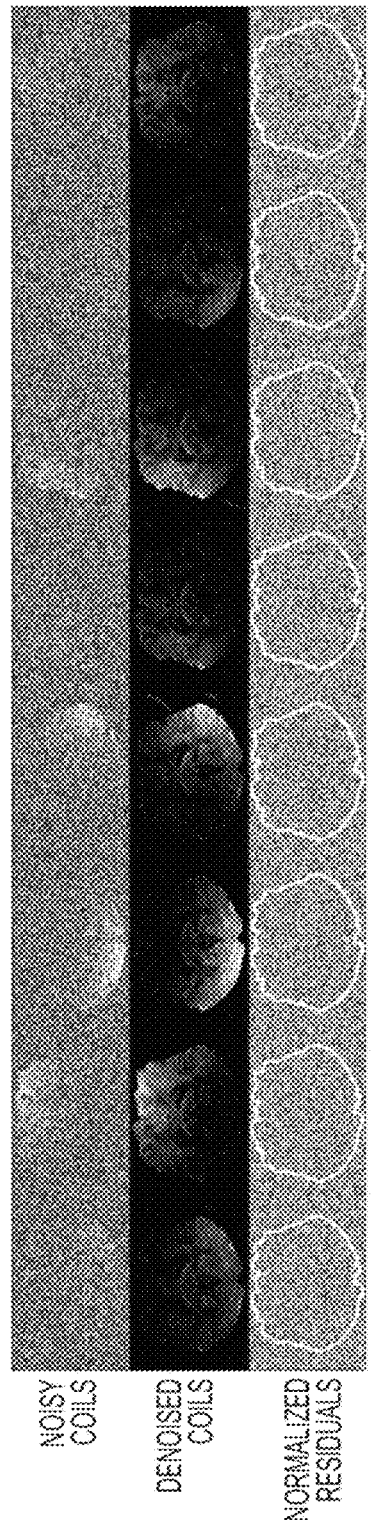
FIG. 2C is a set of exemplary images illustrating noise removal according to an exemplary embodiment of the present disclosure.

FIG. 2C illustrates a set of exemplary images illustrating the noise removal according to an exemplary embodiment of the present disclosure. The jointly RMT-denoised coil images shown in FIG. 2C (e.g., in the decorrelated basis) for the same diffusion contrast (e.g., direction), and the corresponding normalized residuals $r=(\chi-\bar{\chi})/\sigma$, with the local noise standard deviation a estimated by integrating under the identified noise-eigenvalues distribution. (See, e.g., Eq. (1)). No anatomy is seen in the residuals maps.

FIG. 2D shows a set of exemplary graphs corresponding to the exemplary images FIGS. 2A-2C according to an exemplary embodiment of the present disclosure. The histogram (e.g., 205) of the normalized residuals r across all coils, voxels and contrasts, is a straight line with the slope $-\frac{1}{2}$ in semi-log scale, corresponding to a perfectly Gaussian statistics $p(r) \sim e^{-r^2/2}$ (e.g., line 210), down to $r^2$=25 or 1 ppm in the tail, for example, corresponding to a 5σ precision of separating pure noise from the signal. Evaluating the pure-noise statistics of the removed residuals against the known noise distribution (e.g., Gaussian), can be a beneficial quality control procedure for the denoising procedure.

Figure 3A:
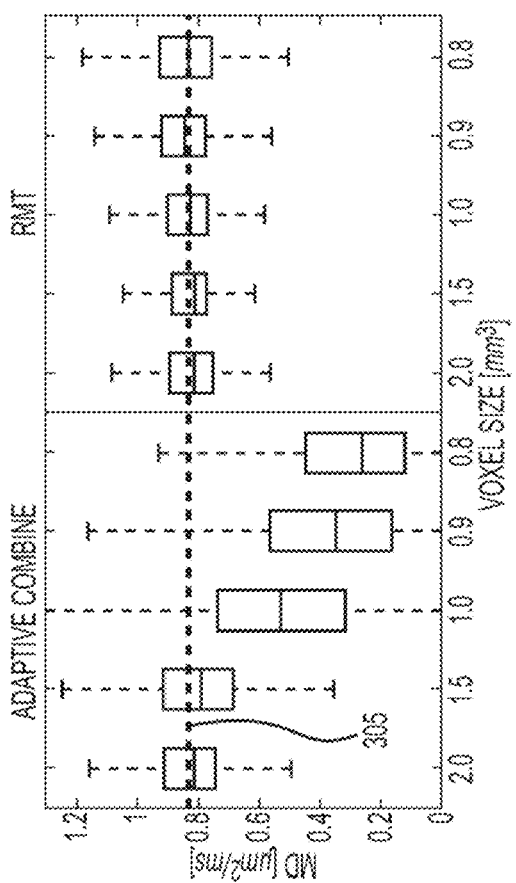
FIG. 3A is a set of exemplary parametric maps for mean diffusivity according to an exemplary embodiment of the present disclosure.
Figure 3B:
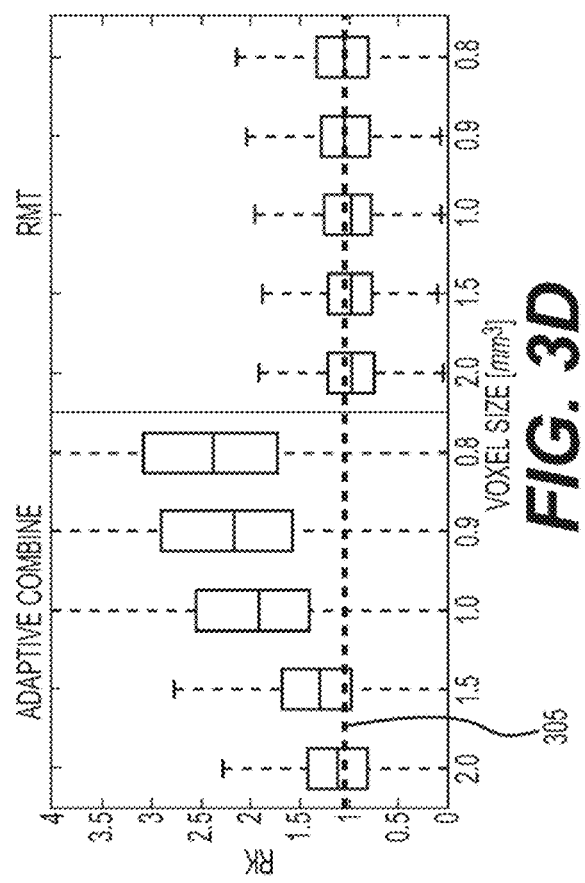
FIG. 3B is an exemplary boxplot for a mean diffusivity for an adaptive combine and random matrix theory according to an exemplary embodiment of the present disclosure.
Figure 3C:
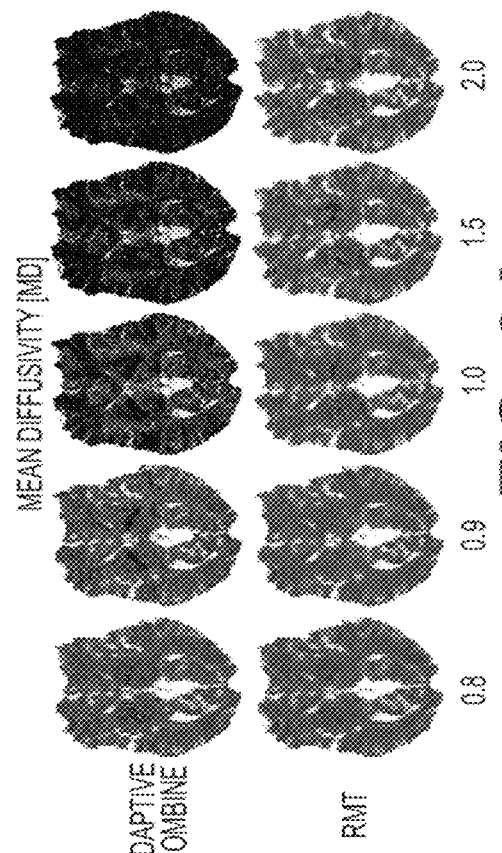
FIG. 3C is a set of exemplary parametric maps for radial kurtosis according to an exemplary embodiment of the present disclosure.
Figure 3D:
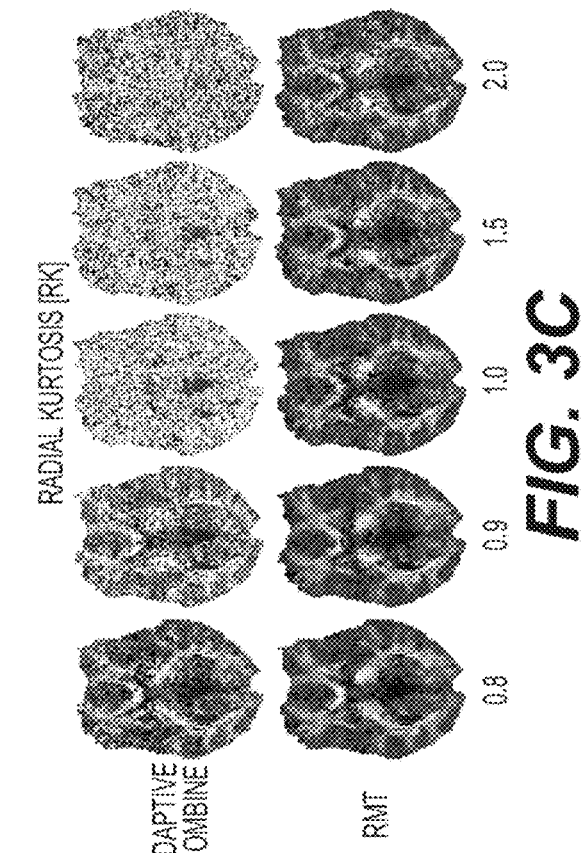
FIG. 3D is an exemplary boxplot for s radial kurtosis for the adaptive combine and random matrix theory according to an exemplary embodiment of the present disclosure.

FIG. 3A illustrates a set of exemplary parametric maps for the mean diffusivity according to standard adaptive combine image reconstruction, and according to an exemplary embodiment of the present disclosure. FIG. 3B shows an exemplary boxplot for the mean diffusivity for adaptive combine and random matrix theory according to an exemplary embodiment of the present disclosure. FIG. 3C shows a set of exemplary parametric maps for the radial kurtosis according to standard adaptive combine image reconstruction, and according to an exemplary embodiment of the present disclosure. FIG. 3D shows an exemplary boxplot for radial kurtosis for the adaptive combine and random matrix theory according to an exemplary embodiment of the present disclosure.

Maps of mean diffusivity ("MD") and radial kurtosis ("RK") are shown across five isotropic spatial resolutions [0.8, 0.9, 1.0, 1.5, 2.0] for AC and RMT. (See, e.g., exemplary images shown in FIGS. 3A and 3C). Boxplots for each exemplary method across the anterior limb of the internal capsule ("ALIC") are shown in FIGS. 3B and 3D. A dashed line 305 is drawn across MD and RK box-plots representing the median of RMT at 2.0 mm isotropic resolution as the ground truth, since the SNR for this resolution is sufficiently high, such that the RMT and AC values coincide. For smaller voxels, Rician bias results in a strong under-estimation of diffusivity, and over-estimation of kurtosis.

FIG. 4A shows a set of exemplary diffusion-weighted images for the adaptive combine and radial matrix theory according to an exemplary embodiment of the present disclosure. Exemplary diffusion-weighted images are shown for the adaptive combine ("AC") and RMT reconstructions on the water phantom. The AC images drown in the Rician noise, while the RMT reconstructed images are visible down to very strong diffusion weighting. FIG. 4B shows an exemplary graph illustrating a measured normalized diffusion-weighted signal $S(b)/S_0$ in the semilog-plot according to an exemplary embodiment of the present disclosure for adaptive-combine (e.g., line 405) and RMT (line 410). A monoexponential $S(b)/S_0$ (a straight-line in semi-log axes) can be indicative of Gaussian diffusion in water, while the deviation from the line can indicate the Rician noise floor proportional to the noise level. RMT-based reconstruction reduces the Rician floor by over 10-fold relative to the state-of-the-art adaptive-combine. FIG. 4C shows an exemplary histogram of mean diffusivity according to an exemplary embodiment of the present disclosure. The exemplary histogram of mean diffusivity (e.g., calculated from b-values up to 1000 s/mm$^2$ to minimize Rician bias) shows a 5-fold increase in the precision. (See e.g., Table I below).

Figure 5A:
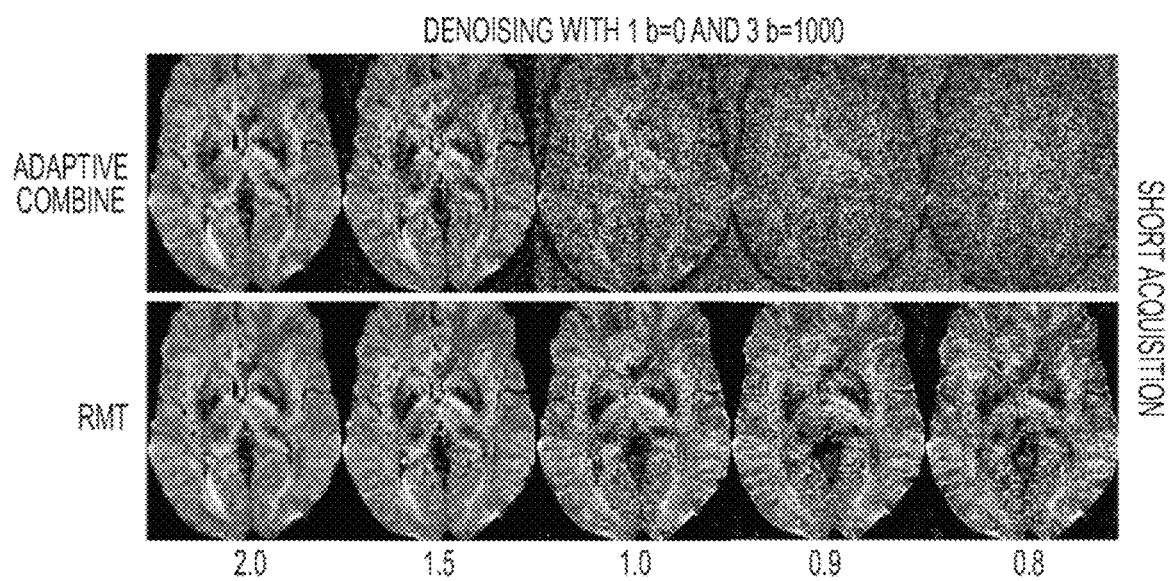
FIG. 5A is a set of exemplary images for a short image acquisition for the adaptive combine and radial matrix theory according to an exemplary embodiment of the present disclosure.
Figure 5B:
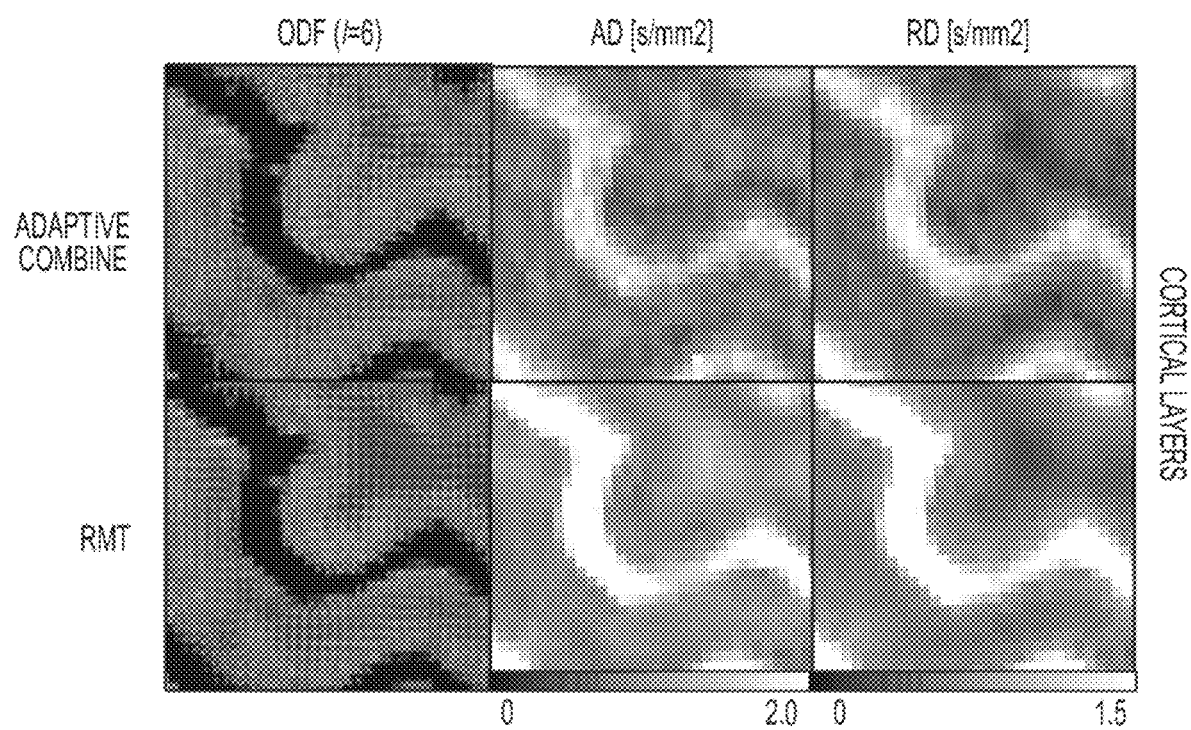
FIG. 5B is set of exemplary reconstructed images for cortical layers for the adaptive combine and radial matrix theory according to an exemplary embodiment of the present disclosure.
Figure 5C:
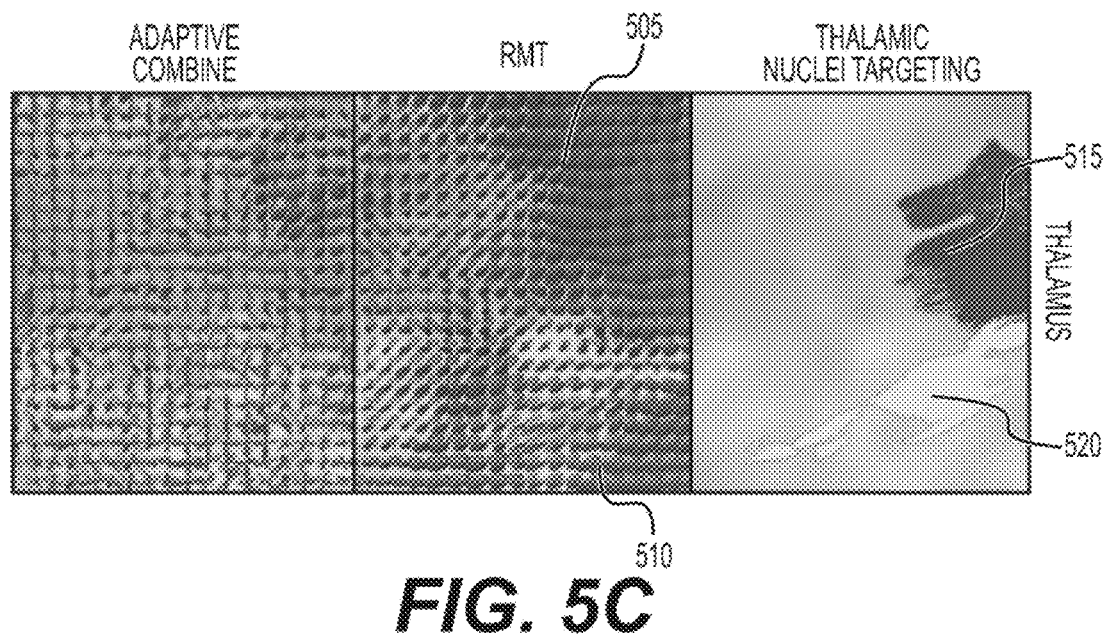
FIG. 5C is a set of reconstructed images of the thalamus for the adaptive combine and radial matrix theory and a thalamic nuclei targeting according to an exemplary embodiment of the present disclosure.
Figure 5D:
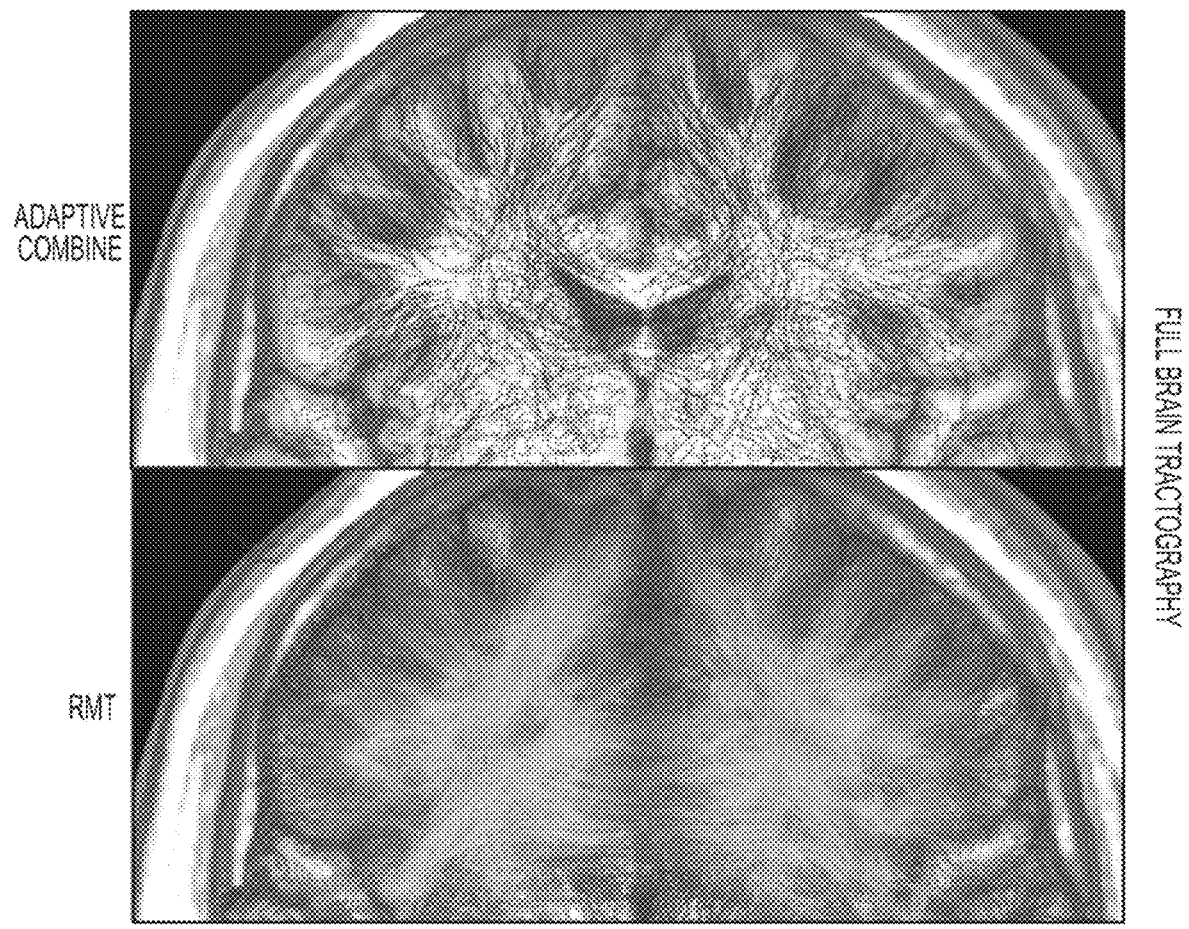
FIG. 5D is a set of exemplary reconstructed images of a full brain tractography for the adaptive combine and radial matrix theory according to an exemplary embodiment of the present disclosure.

FIG. 5A shows illustrates a set of exemplary images for a short acquisition for the adaptive combine and random matrix theory according to an exemplary embodiment of the present disclosure. FIG. 5B shows a set of exemplary reconstructed images for cortical layers for the adaptive combine and random matrix theory according to an exemplary embodiment of the present disclosure. FIG. 5C shows illustrates a set of reconstructed images of the thalamus and thalamic nuclei targeting for the adaptive combine, and random matrix theory according to an exemplary embodiment of the present disclosure. FIG. 5D shows a set of reconstructed images of full brain tractography for the standard adaptive combine and for the random matrix theory denoising+reconstruction, according to an exemplary embodiment of the present disclosure.

Exemplary model-based microstructure mapping approaches (see, e.g., Reference 37), enabled by the improved SNR according to exemplary embodiments of the present disclosure, can reveal micrometer-scale cellular biophysics and geometry otherwise inaccessible by the millimeter-scale imaging resolution. Microstructure mapping can utilize, for example, selective suppression of the diffusion-weighted signal. Higher dynamic range to study the diffusion signal attenuation unlocks specificity towards cellular-level biophysics, and resolving white-matter crossings for the fiber tractography relevant for the preoperative planning.

In each of the exemplary applications shown in FIGS. 5A-5D, the standard adaptive combine ("AC") and the RMT reconstructions are compared. The first application (see e.g., FIG. 5A) achieves sub-mm clinical resolution with very small number $N_c$=4 of acquired diffusion contrasts, by boosting the redundancy using large number of RF coils, $N_r$=16, and the voxel patch size $N_x$=5×3×3=45, such that the covariance matrix of the size 4*16×45 is large enough for RMT. This example underscores the key concept of the present disclosure, the need to utilize the signals of individual RF coils in the RMT denoising, since performing adaptive combine reconstruction for each diffusion-weighted image would yield the 2-dimensional (rank-2-tensor) measurement matrix of a small size, $N_c \times N_x$=4×45, which is not enough for PCA-based denoising, since its matrix rank cannot exceed 4. The result of the image reconstruction according to the standard AC, and according to an exemplary embodiment of the present disclosure utilizing the 3-dimensional measurement reshaped into the matrix of size $(N_c \cdot N_r) \times N_x$, is shown for a single direction at b=1000 s/mm$^2$ across 5 isotropic spatial resolutions [0.8, 0.9, 1.0, 1.5, 2.0].

The remaining applications (see, e.g., FIGS. 5B-5D) are obtained from a full-brain acquisition at 0.8 mm isotropic voxels (Experiment 3 in the Methods section). As shown in FIG. 5B, only after the RMT reconstruction (current embodiment of the present disclosure) can the cortical layers in the motor and somatosensory cortex be observed, as exemplified by the increased coherent crossings from the orientation distribution function ("ODF") for 6th-order spherical harmonics (l=6), and the contrast observed on axial, AD, and radial, RD, diffusivities derived from the diffusion tensor. The values of the CSF diffusivities after AC are ~1 μm$^2$/ms, are far too small to resemble diffusion through nearly free-water; however, the corresponding CSF diffusivities after the RMT reconstruction can be ~2.5 μm$^2$/ms, which are sufficiently close to that of free water at body temperature (3 μm$^2$/ms).

As shown in FIG. 5C, RMT can facilitate the observation of thalamic nuclei including the ventral intermediate nucleus of the thalamus ("VIM"). The VIM can be easily seen on the RMT-reconstructed maps as the sparse area between the areas 505 and 510 dark and bright ODFs. Moreover, RMT had sufficient SNR to identify the medial leminiscus (e.g., element 515) and pyramidal tract (e.g., element 520) pathways to deduce the location of the VIM, which can occur at their intersection. Standard AC reconstruction was unable to resolve these pathways and yielded unusable fiber orientations "squashed" by the Rician floor with such small voxels. As shown in FIG. 5D, RMT can facilitate full-brain tractography with 0.8 mm isotropic voxels. 200,000 random seed points were generated across a white matter mask for both AC and RMT tracts (using standard open-source package mrtrix3.0; utility tensor_prob).

The exemplary parametric maps and boxplots shown in FIGS. 3A-3D illustrate that the exemplary RMT procedure can provide unbiased estimation of mean diffusivity and kurtosis (e.g., a higher-order metric). The positive Rician noise floor heavily reduces the estimated mean diffusivity and increases the kurtosis, as expected for the standard adaptive-combine ("AC") reconstruction (see, e.g., Reference 36); the RMT reconstruction holds its ground remarkably well down to sub-millimeter resolutions. Table I below quantifies the increase in precision due to RMT, by evaluating the relative error (e.g., coefficient of variation CV, defined as a ratio of the standard deviation over the mean, calculated over a region of interest) for the mean diffusivity (e.g., defined as ⅓ of the trace of the diffusion tensor). CV can be improved by almost 10-fold for the highest-resolutions. In FIGS. 4A-4C, these effects of bias and precision can be validated on a water phantom, where the RMT reconstruction increases the dynamic range of diffusion-weighted signal by an order of magnitude.

The exemplary RMT-based reconstruction can apply to any redundant acquisition, such as diffusion, perfusion, fMRI, and any combination of those, and with added simulated noise and artifacts to augment the overall data dimension, provided that they can be acquired/created using the same voxels and sampling patterns to preserve the common noise statistics and benefit from the anatomical redundancy. This observation prompts the development of RF coils with a largest possible number of elements, as well as a joint optimization of various imaging protocols to acquire all clinically utilized MR contrasts in the same manner.

TABLE I

Coefficient of variation for the mean diffusivity, and the ratio by which it decreases using RMT reconstruction, in different regions of interest from the acquisition shown in FIGS. 1 and 3, and in water phantom (e.g., FIG. 4). For the highest resolutions, the measurement precision increases by about 10-fold.

| ROI | Method | 2.0 mm | 1.5 mm | 1.0 mm | 0.9 mm | 0.8 mm |
|---|---|---|---|---|---|---|
| White Matter | AC | 0.480 | 0.493 | 0.803 | 1.291 | 2.566 |
|  | RMT | 0.460 | 0.425 | 0.383 | 0.37 | 0.377 |
|  | CV Ratio | 1.043 | 1.161 | 2.093 | 3.486 | 6.804 |
| ALIC | AC | 0.137 | 0.212 | 0.599 | 0.866 | 1.266 |
|  | RMT | 0.072 | 0.075 | 0.074 | 0.090 | 0.134 |
|  | CV Ratio | 1.889 | 2.850 | 8.069 | 9.612 | 9.433 |
| Thalamic Radiation | AC | 0.409 | 0.419 | 0.572 | 0.975 | 1.911 |
|  | RMT | 0.396 | 0.360 | 0.228 | 0.225 | 0.240 |
|  | CV Ratio | 1.031 | 1.163 | 2.509 | 4.337 | 7.957 |
| Phantom | AC | 0.059 |  |  |  |  |
|  | RMT | 0.012 |  |  |  |  |
|  | CV Ratio | 4.917 |  |  |  |  |

Exemplary Methods
Exemplary RMT Reconstruction Steps

Exemplary Coil noise Decorrelation. Due to the variability of resistivities across coil elements, and overlap of coil sensitivity profiles, each coil can have its own noise level, leading to different diagonal elements of matrix $\Psi$ in Eq. (2), and there can be correlations between them, causing the off-diagonal matrix elements. To decorrelate the noise, various exemplary coil combinations can be formed, for example, based on:

$$\tilde{\chi}_{xcr} = \sum_{r'=1}^{N_r} (\Psi^{-1/2})_{rr'} \chi_{xcr'}, \Psi^{-1/2} = U\psi^{-1/2}U', \quad (4)$$

where $\psi = U^T\Psi U$ can be the diagonal matrix of eigenvalues of $\psi$ after the unitary rotation U. In the rotated basis, coils have Gaussian noise, and MP theory applies to the rank-3-tensor (e.g., 3-dimensional) "rotated" object $\tilde{\chi}$, enabling the objective identification and removal of the noise as described above, by identifying the pure-noise distribution, for example, Eq. (1), from the suitably-defined covariance matrix constructed from $\tilde{\chi}$, followed by an appropriate thresholding of eigenvalues (e.g., hard or soft thresholding near the noise edge).

Exemplary Nyquist Ghost Correction. An exemplary Nyquist ghost correction procedure can be performed by adjusting odd/even lines through the application of a linear phase that can be estimated from line scans. (See, e.g., Reference 38). A linear phase correction can preserve the noise-statistics, and increase spatial redundancy during the phase estimation and denoising steps; however, the residual Nyquist ghost can still remain in the images. Non-linear procedures towards phase-correction for the elimination of Nyquist ghost (see, e.g., Reference 39), can be applied after denoising as they can strongly influence the noise-statistics.

Exemplary Merging k-Space Lines to Preserve Noise statistics in Case of Undersampling. To achieve faster scan times as well as shorter echo times (e.g., for higher SNR due to $T_2$-weighting), modern MRI images can be acquired with missing MRI k-space lines. It can be beneficial for the RMT denoising to utilize the spatial redundancy principle (see, e.g., Reference 40), according to which the number of significant components can be greatly reduced if all the voxels in a patch have similar signals. In the extreme case when each voxel's ground truth signal can be the same within a patch, the number of significant components P=1 irrespective of the complexity of the contrasts, in which case it can be beneficial to average over all voxels in a patch. RMT can provide an automatic manner to uncover such spatial redundancy and perform this averaging. As the spatial redundancy exists in the image domain, the rank-3 object $\chi_{xcr}$ can be formed, RMT denoising can be used by the exemplary system, method and computer-accessible medium.

However, the white noise statistics can generally be corrupted after utilizing parallel imaging and k-space filling methods (e.g., Sensitivity Encoding ("SENSE") (see, e.g., Reference 41), GeneRalized Autocalibrating Partial Parallel Acquisition ("GRAPPA") (see, e.g., Reference 42), Efficient L1SPIRiT Reconstruction ("ESPIRiT") (see, e.g., Reference 43), or neural nets (see, e.g., References 22 and 23). To perform RMT denoising prior to k-space filling, only the acquired k-space lines may be used. Filling the un-acquired data with zeros can mostly preserve the phase; however, introducing zeros into the Fourier transform can cause undersampling artifacts in the image domain: such as, but not limited to, aliasing of both signal and noise for regular undersampling, and interpolation/Gibbs ringing for the partial Fourier transform. (See e.g., FIGS. 6A-6D, 8A-8G and 11A-11G). Performing naive Fourier transform with zero-filled lines distorts the Nyquist-Johnson noise statistics and obscures the MP distribution. (See e.g., FIGS. 6A-6D). To preserve the noise statistics, the Fourier transform can be performed on all of the acquired lines by merging them together, thereby excluding all un-acquired lines (e.g., zeros) from the transform. In this manner, the spatial dimension of the resulting inverse Fourier transform equals to the number of acquired lines.

For other exemplary undersampling patterns including, non-Cartesian undersamplings (e.g., radial or spiral undersamplings), a similarly suitable merging procedure can be utilized, such that the spatial dimension of the resulting inverse Fourier transform can be, for example, the same as that of the number of acquired k-space points. Another variant of the arranging, for example, the rank-3 object $\chi_{xcr}$ can be to operate in the k-space directly, which can include considering the rank-3 measurement matrix $\chi_{kcr}$ where the index k numbers the k-space points. The redundancy directly in the k-space can be used, and the remaining denoising procedures, such as forming the rank-2 (e.g., 2-dimensional) covariance matrix $X_{aa'}$ based on $\chi_{kcr}$ can be performed analogously to what was described above. Any equivalent basis or representation, not limited to the k-space or the image space, can be applied to suitably represent the rank-3 measurement object $\chi$ that fundamentally has at least one dimension devoted to selecting the imaging voxels (in any basis). Different generally non-local procedures of arranging the imaging-voxel-dimension samplings (e.g., non-local patches in the k-space, or in the image space, for example, using non-local means methods, based on some objective similarity criterion; or belonging to anatomically homogeneous regions of interest) can be utilized to select the most redundant set of measurements for the subsequent denoising procedure.

Figure 6A:
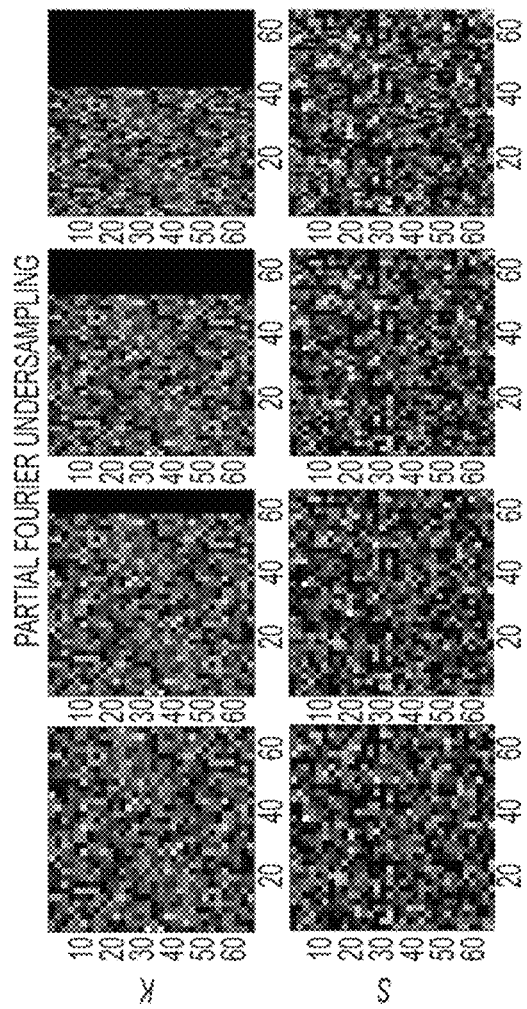
FIG. 6A is a set of exemplary images illustrating a partial Fourier undersampling according to an exemplary embodiment of the present disclosure.
Figure 6B:
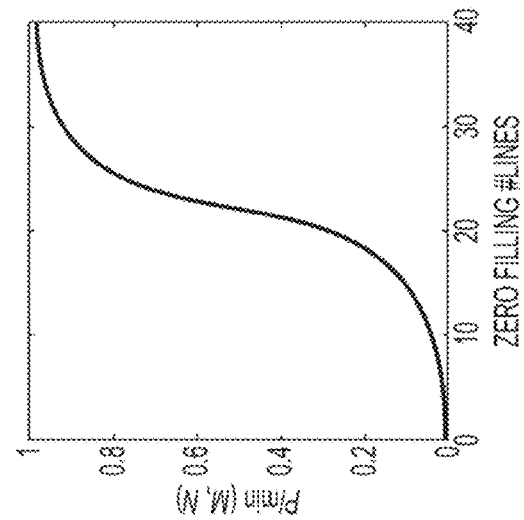
FIG. 6B is an exemplary graph illustrating the number of filling #lines for FIG. 6A according to an exemplary embodiment of the present disclosure.
Figure 6C:
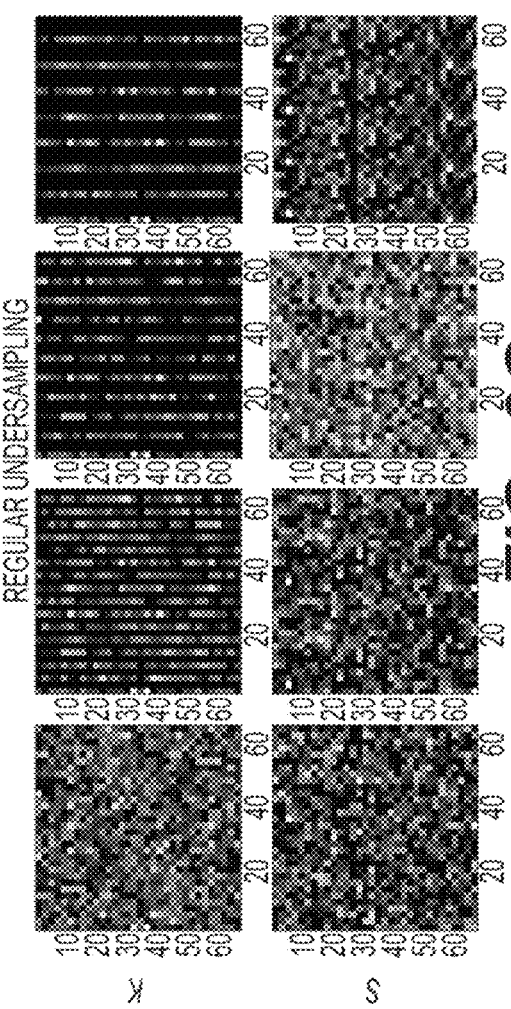
FIG. 6C is a set of exemplary images illustrating a regular undersampling according to an exemplary embodiment of the present disclosure.
Figure 6D:
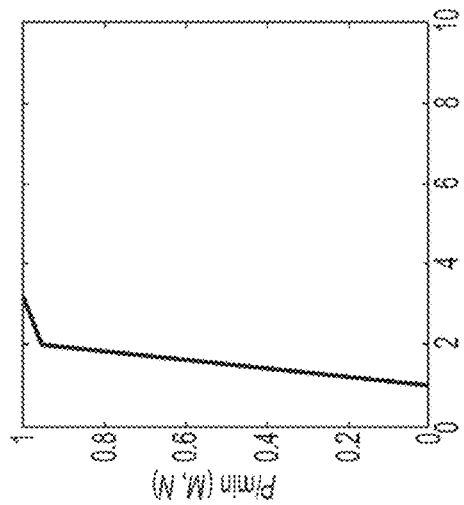
FIG. 6D is an exemplary graph illustrating the number of filling #lines for FIG. 6C according to an exemplary embodiment of the present disclosure.

FIG. 6A shows a set of exemplary images illustrating a partial Fourier undersampling according to an exemplary embodiment of the present disclosure. FIG. 6B illustrates an exemplary graph illustrating the number of filling lines for FIG. 6A according to an exemplary embodiment of the present disclosure. FIG. 6C shows a set of exemplary images illustrating a regular undersampling according to an exemplary embodiment of the present disclosure. FIG. 6D shows an exemplary graph illustrating the number of filling lines for FIG. 6C according to an exemplary embodiment of the present disclosure. For example, 1500 samples of a 64×64 unit noise images were generated and the corresponding k-space, K, and image-domain, S, are displayed for various degrees of partial Fourier and regular undersampling patterns. Without undersampling, RMT accurately concludes that the image is entirely noise, and there are no significant components in the image, P=0. With greater undersampling, performing inverse Fourier transform with zero-filled missing lines, causes the noise-correlations to appear as significant components, such that the random fluctuations in S begin to resemble some coherent structure. Moreover, the ratio between P and the rank of the matrix, P/min(M,N) (e.g., an indicator of the fraction of components that can be removed) approaches 1, indicating that no MP noise distribution is detected. This illustrates that introducing any regular undersampling causes P/min(M,N)→1 very quickly, if zero-filling of the missing lines is used to perform the inverse Fourier transform.

Figure 7A:
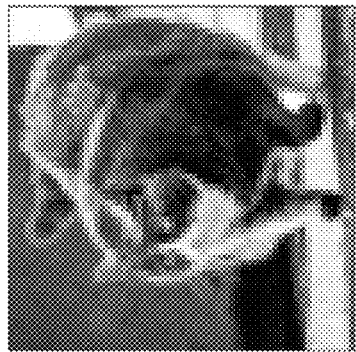
FIG. 7A is an exemplary image of a simulated reconstruction according to an exemplary embodiment of the present disclosure.
Figure 7B:
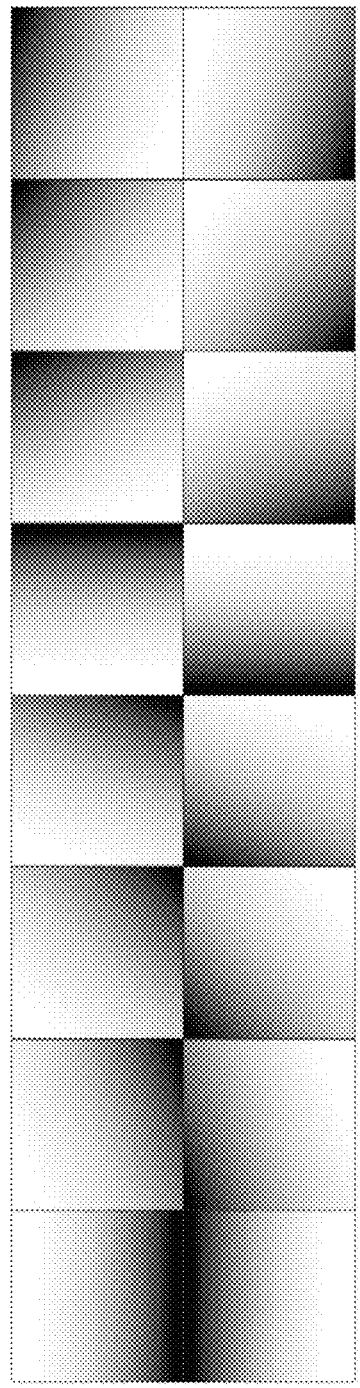
FIG. 7B is a set of exemplary diffusion weighted images according to an exemplary embodiment of the present disclosure.

Complex-valued coil diffusion weighted images were generated using the diffusivity map, D. FIG. 7A shows an exemplary image of a simulated reconstruction according to an exemplary embodiment of the present disclosure, with linear coil sensitivities, $C(x)$, and linear phase, $Ø(x)$, varying over 16 coil elements. FIG. 7B illustrates a set of diffusion weighted images according to an exemplary embodiment of the present disclosure. $S(b, x)=S_0 \cdot C(x)e^{-bD(x)-iØ(x)}$, where $S_0$ is constant over the image, determining the SNR level. $N_c=104$ diffusion weighted images were generated with [4, 20, 80] averages for b=[50, 500, 1000] s/mm², respectively. Uncorrelated complex noise with unit $\sigma=1$ is added, $S_n(b)=S(b)+\in'+i\in''$; here the noise is drawn as $\in', \in'' \sim \mathcal{N}(0,1)$ (unit normal distribution with zero mean).

Figures 8A, 8B, 8C, 8D:
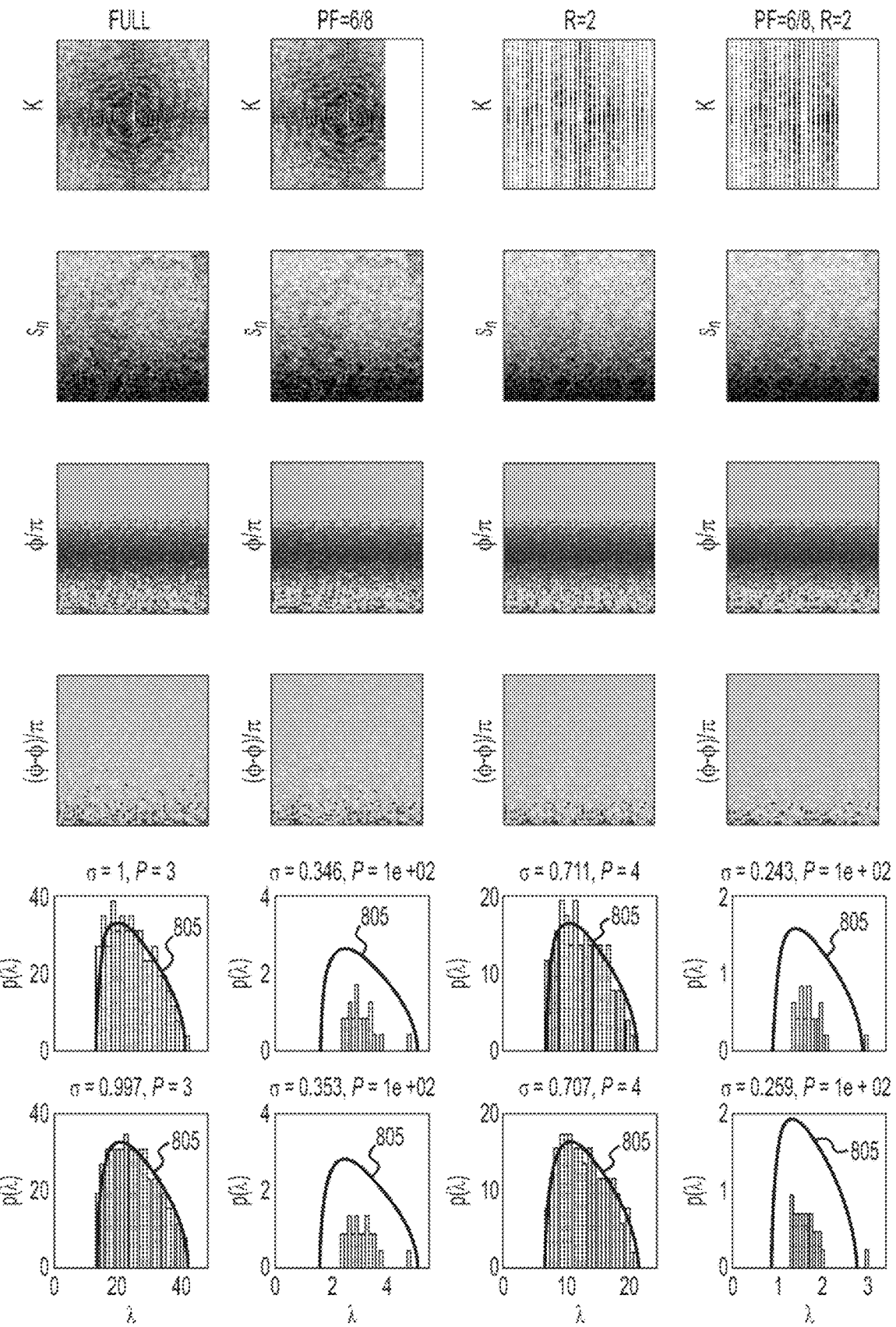
FIGS. 8A-8G are sets of exemplary reconstructed images and corresponding histograms according to an exemplary embodiment of the present disclosure.
Figures 8E, 8F, 8G:
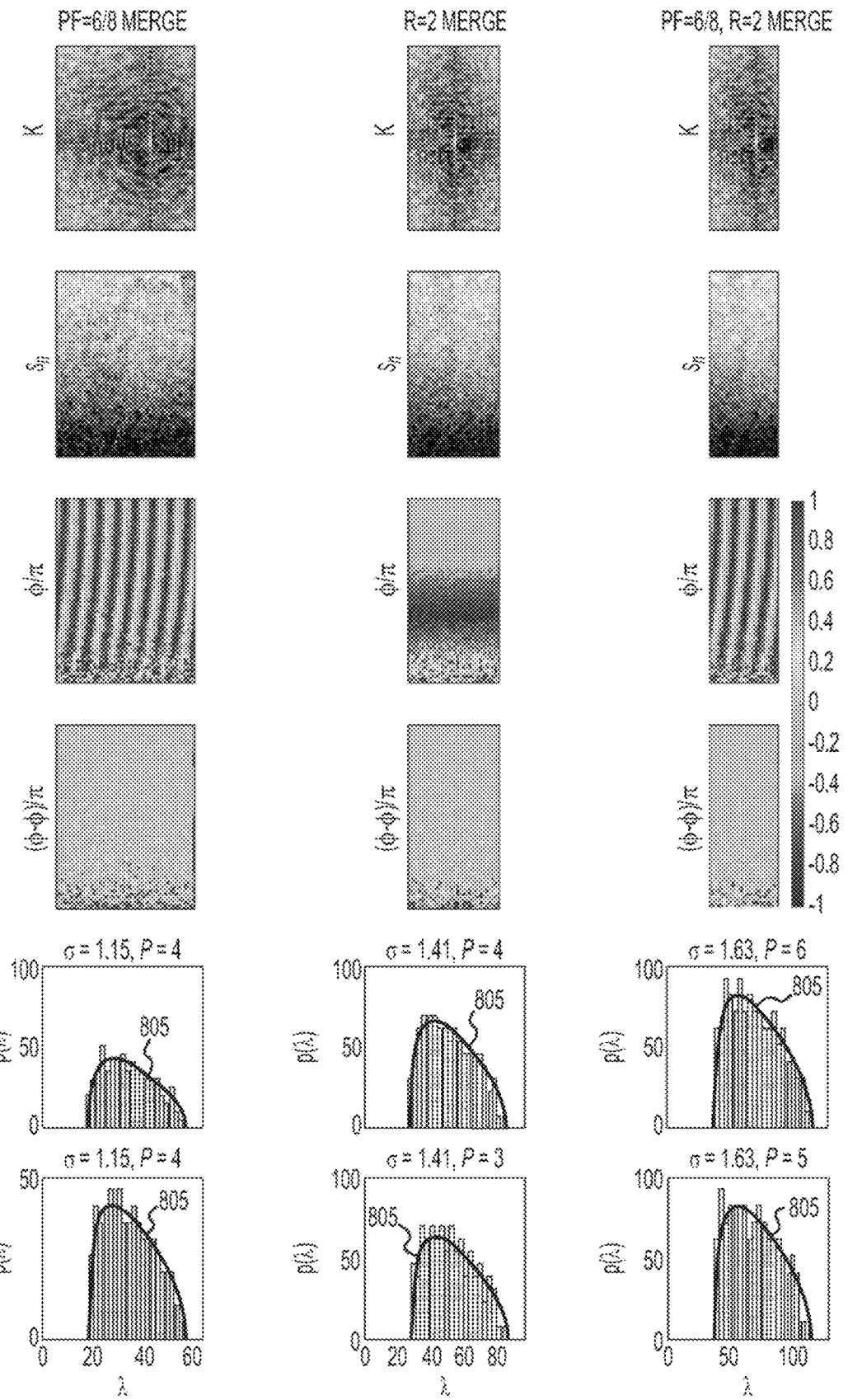

FIGS. 8A-8G show set of exemplary reconstructed images and corresponding histograms according to an exemplary embodiment of the present disclosure. The first 4 rows from top to bottom, show an individual noisy contrast image (in this case, a diffusion-weighted image) for an individual coil for the k-space, K; image space, $S_n$; normalized phase, $Ø/\pi$, and the normalized phase $(Ø-\hat{Ø})/\pi$ after phase unwinding via the estimated phase, $\hat{Ø}$. The estimated phase was determined from the highest principal component from a matrix with a 2-dimensional sliding window 7×7 (e.g., within an image slice) vs all coils and contrasts. The last two rows show histograms of the eigenvalues overlapping with the estimate of the MP distribution (e.g., 805) and the noise level, a, and number of significant principal components outside of the noise distribution, P, as described above by fitting Eq. (1) to the histograms. These MP distributions were determined using a 3-dimensional $N_x=5×5×5$ patch at the center of the image. FIG. 3A illustrates a fully sampled example, FIG. 8B illustrates an undersampled acquisition with partial Fourier=6/8, FIG. 8C illustrates undersampled acquisition regularly with R=2, FIG. 8D illustrates undersampled acquisition with both partial Fourier=6/8 and regularly with R=2. FIG. 8E-8G illustrates partial Fourier, regular, and partial Fourier+regular undersampling after merging the acquired lines, and excluding all zeros from the Fourier transform. This exemplary procedure can preserve the Nyquist-Johnson noise-statistics, and can dramatically lower P, but can introduce a strong phase shift in the case of partial Fourier. The increase in P due to this phase shift can be further undone by unwinding via estimating the local phase $\hat{Ø}$ as described above. Note that the noise levels estimated in FIGS. 8E-8G with MP theory can correctly correspond to the numbers of sampled lines: $\sqrt{8/6}\approx1.15$, $\sqrt{2}\approx1.41$, and $\sqrt{2\cdot8/6}\approx1.63$.

Figures 9A, 9B, 9C, 9D:
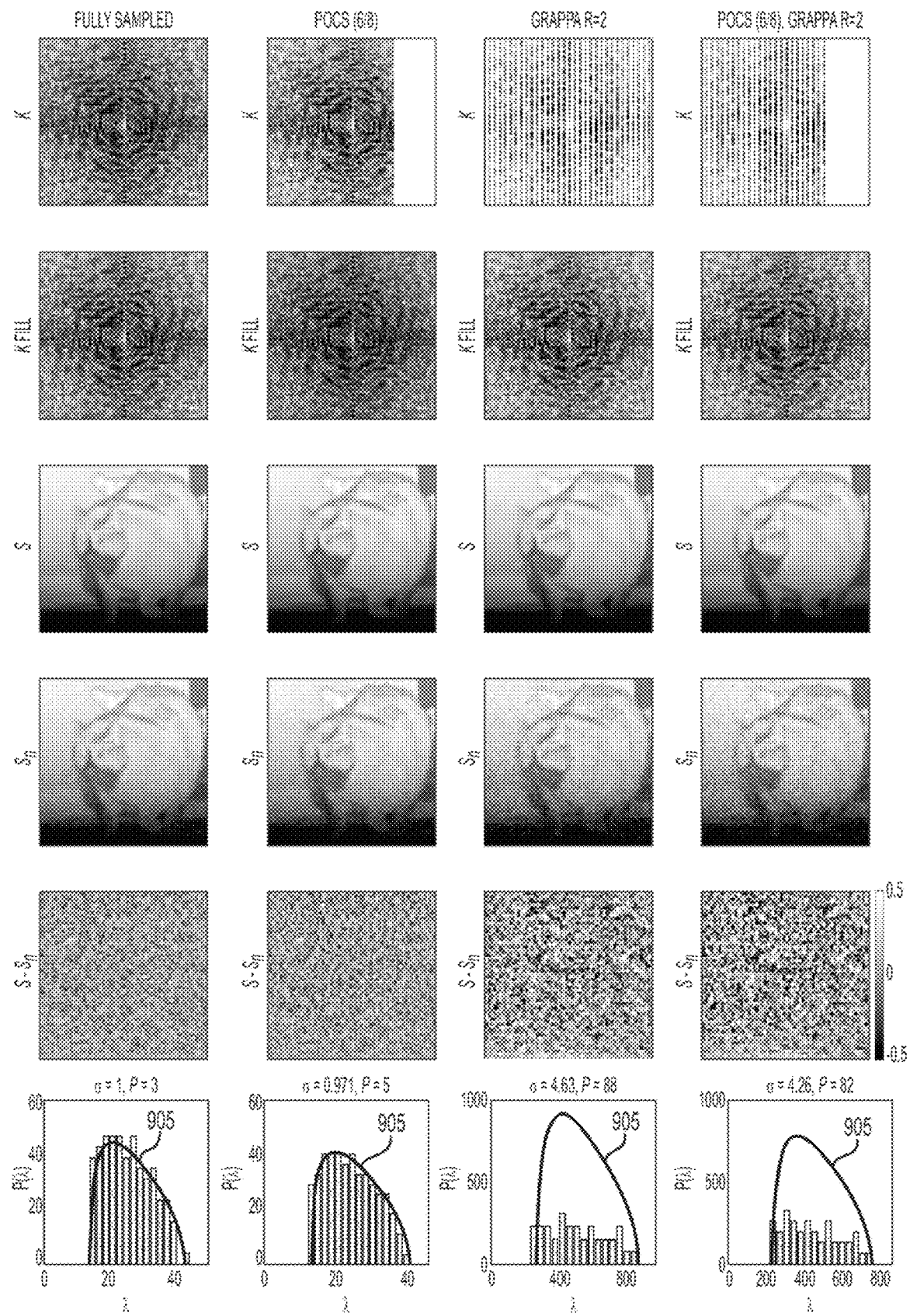
FIGS. 9A-9D are sets of exemplary reconstructed images according to an exemplary embodiment of the present disclosure.

FIGS. 9A-9D show a set of exemplary reconstructed images according to an exemplary embodiment of the present disclosure. The first 5 rows from top to bottom, show undersampled k-space, filled k-space with the respective algorithm, the reconstructed noiseless diffusion-weighted signal, S(b) for b=1000, the reconstructed noisy diffusion-weighted signal, $S_n(b)$, the residuals, $S-S_n$, and the fit of the MP distribution, taken over the same central 5×5×5 patch as in FIG. 8. FIG. 9A shows fully sampled k-space, FIG. 9B shows the POCS reconstruction on partial Fourier 6/8, FIG. 9C shows the GRAPPA reconstruction on R=2, and FIG. 9D shows GRAPPA+POCS reconstruction on partial Fourier and regularly undersampled data. All k-space filling methods result in some degree of deviation from the ideal MP-distribution, thus an increase in P, and a non-unit σ—especially for the regular undersampling. Curve 905 illustrates a fit of MP distribution (e.g., based on Eq. (1)), to the histogram of the PCA eigenvalues. The principal components which fall under curve 905 correspond to pure noise and are to be removed as part of the RMT procedure.

Figure 10A:
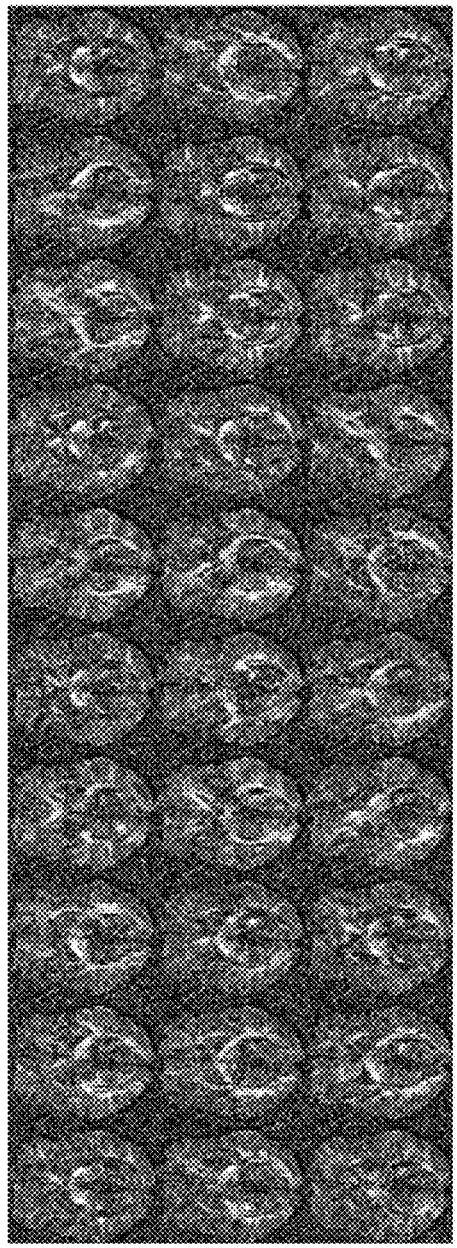
FIGS. 10A and 10B are sets of exemplary images illustrating the adaptive-combine and random matrix theory reconstructions according to an exemplary embodiment of the present disclosure.
Figure 10B:
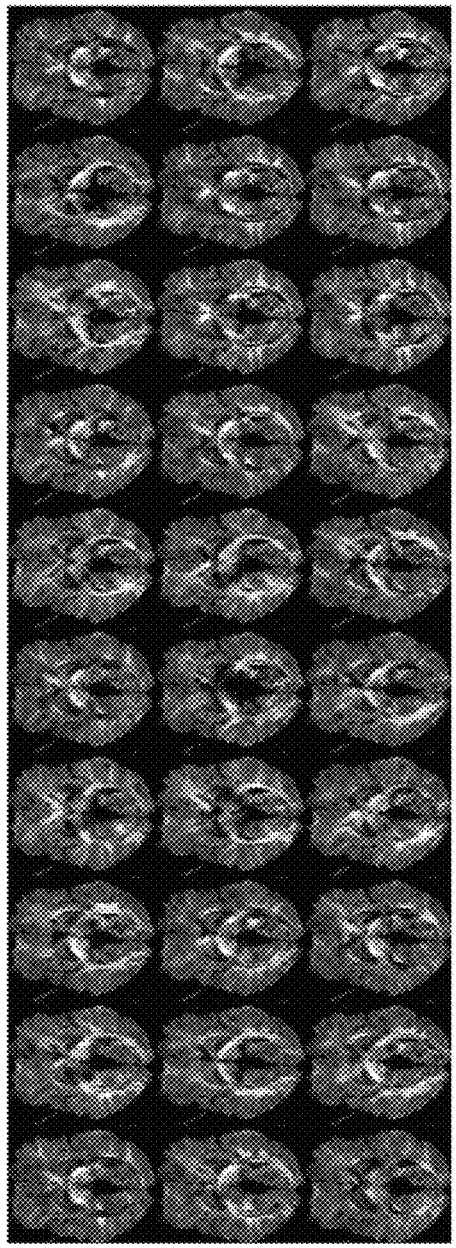
Figure 10C:
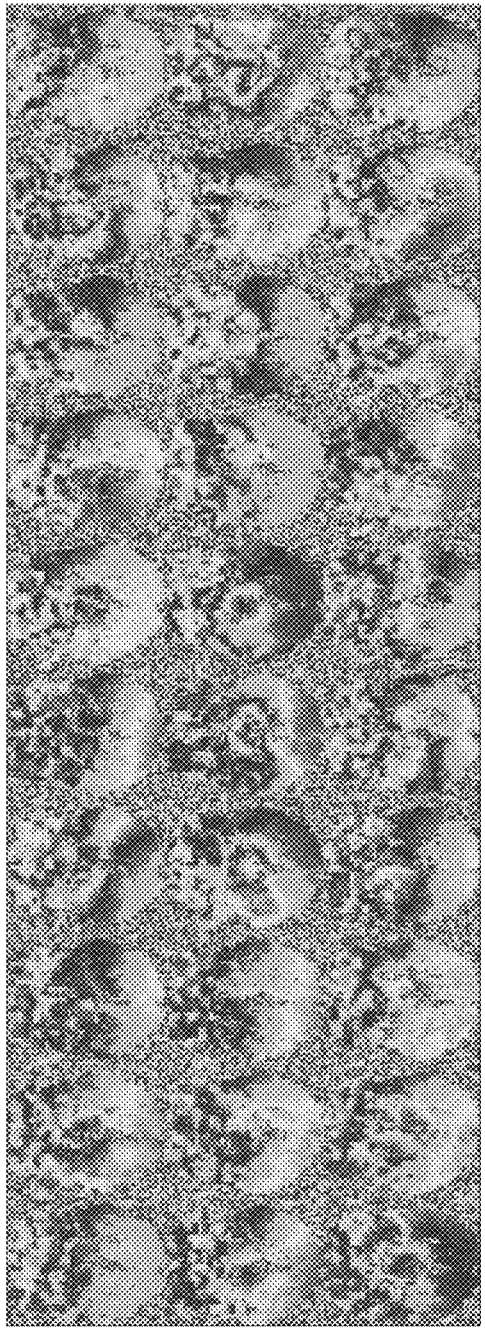
FIGS. 10C and 10D are sets of exemplary images illustrating the adaptive-combine and random matrix theory reconstructions of a phase according to an exemplary embodiment of the present disclosure.
Figure 10D:

FIGS. 10A and 10B show sets of exemplary images illustrating the adaptive-combine and random matrix theory reconstructions of an image magnitude according to an exemplary embodiment of the present disclosure. FIGS. 10C and 10D show sets of exemplary images illustrating the adaptive-combine and random matrix theory reconstructions of a phase according to an exemplary embodiment of the present disclosure. Data from Experiment 2, with 30 directions at b=3000 s/mm², 2.0 mm isotropic resolution, showing AC and RMT reconstructions of the magnitude (e.g., as shown in FIGS. 10A and 10B) and phase (e.g., as shown in FIGS. 10C and 10D). Note the pulsation, characterized by rapid phase shifts, and wrapping at the center of the brain, and velocity/bulk motion, characterized by wrapping across the entirety of the brain, in a particular direction.

Figure 11A:
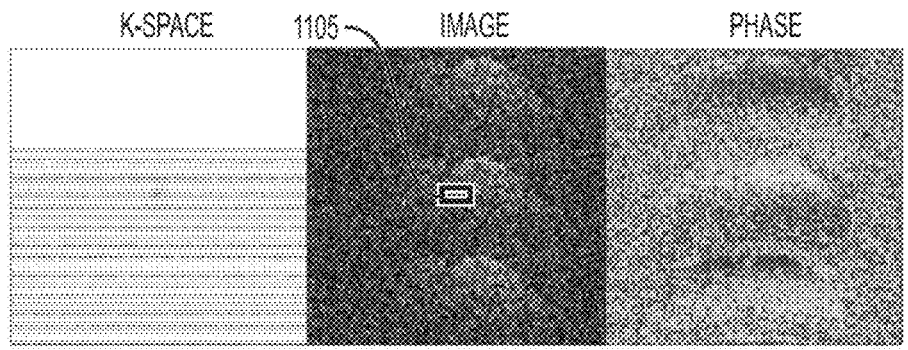
FIG. 11A-11D are exemplary images of a single-direction k-space, magnitude and phase images according to an exemplary embodiment of the present disclosure.

FIG. 11A-11D show exemplary images of a single-direction k-space, magnitude and phase images according to an exemplary embodiment of the present disclosure. FIG. 11E shows a set of exemplary reconstruction images for adaptive combine according to an exemplary embodiment of the present disclosure. FIG. 11F shows a set of exemplary reconstruction images for random matrix theory according to an exemplary embodiment of the present disclosure.

The brain of a 26 y/o male volunteer was imaged using a 64-channel coil on a Siemens 3T Prisma system with 42 coil elements enabled during the scan. The image was undersampled with factor R=3 and partial Fourier factor 6/8, 20 slices around the hippocampus/brainstem were acquired with 1.0 mm isotropic voxels, $T_R=4$ s, $T_E=65$ ms, and acquisition time=1:48. dMRI were acquired with 20 directions at b=500 s/mm² and 2 b=0 images. FIGS. 11A-11D show a single-direction b=500 s/mm² k-space, magnitude and phase images for an individual coil element. The histograms of PCA eigenvalues are determined from the anisotropic patch 1105 of 11×5×3=165 voxels, with more samples taken from the frequency (see, e.g., Reference 11), than from the phase encoding (see, e.g., Reference 5), directions, over 3 slices. RMT denoising was performed based on reshaping the measurement matrix χ according to 165×(42×22). FIG. 11A shows under-sampled data and demonstrates variable phases over the aliased image (e.g., obtained by zero-filling the missing k-space lines), with the corresponding PCA histogram showing no MP distribution and very many (P=132) empirically significant components.

Figure 11B:
Figure 11C:
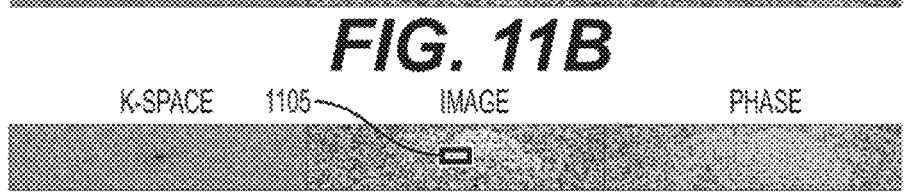

FIG. 11B shows the staking of the acquired k-space lines without zero-filling in-between (to increase the redundancy), and the PCA eigenvalues within the patch closely resemble the ideal MP-distribution with just a handful (P=4) significant components out of 165 total. The phase in each coil varies rapidly over the brain, mainly due to the partial-Fourier, resulting in the off-center k-space peak reminiscent of a velocity encoding. As shown in FIG. 11C, the overall phase is estimated for each slice over a larger 2-dimensional 17×17 patch (e.g., within a slice) and subsequently unwound, resulting in a more precise MP-distribution with even fewer significant components (P=3) obtained by performing RMT denoising on the same 11×5×3 patch (red).

Figure 11D:
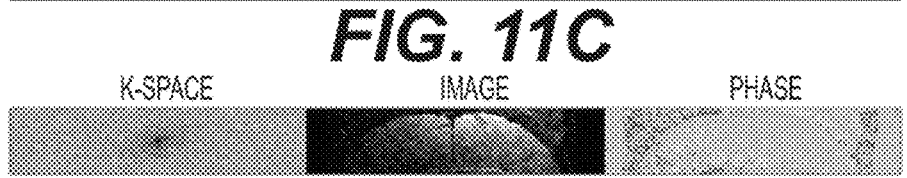
Figure 11E:
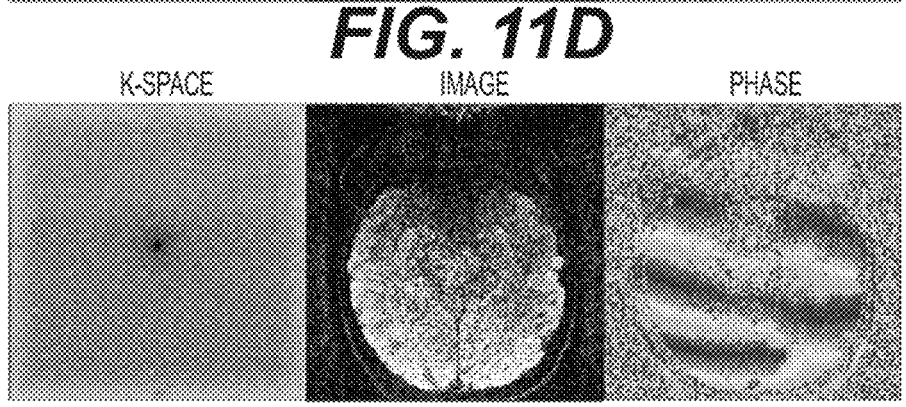
FIG. 11E is a set of exemplary reconstruction images for the adaptive combine according to an exemplary embodiment of the present disclosure.
Figure 11F:
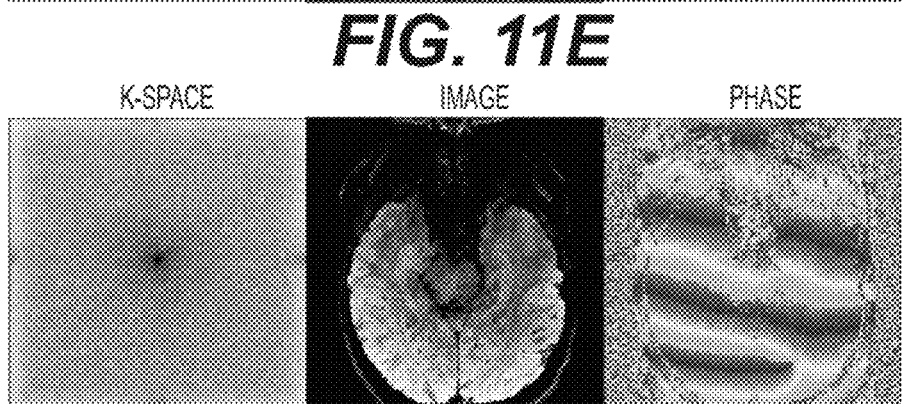
FIG. 11F is a set of exemplary reconstruction images for the random matrix theory according to an exemplary embodiment of the present disclosure.
Figure 11G:
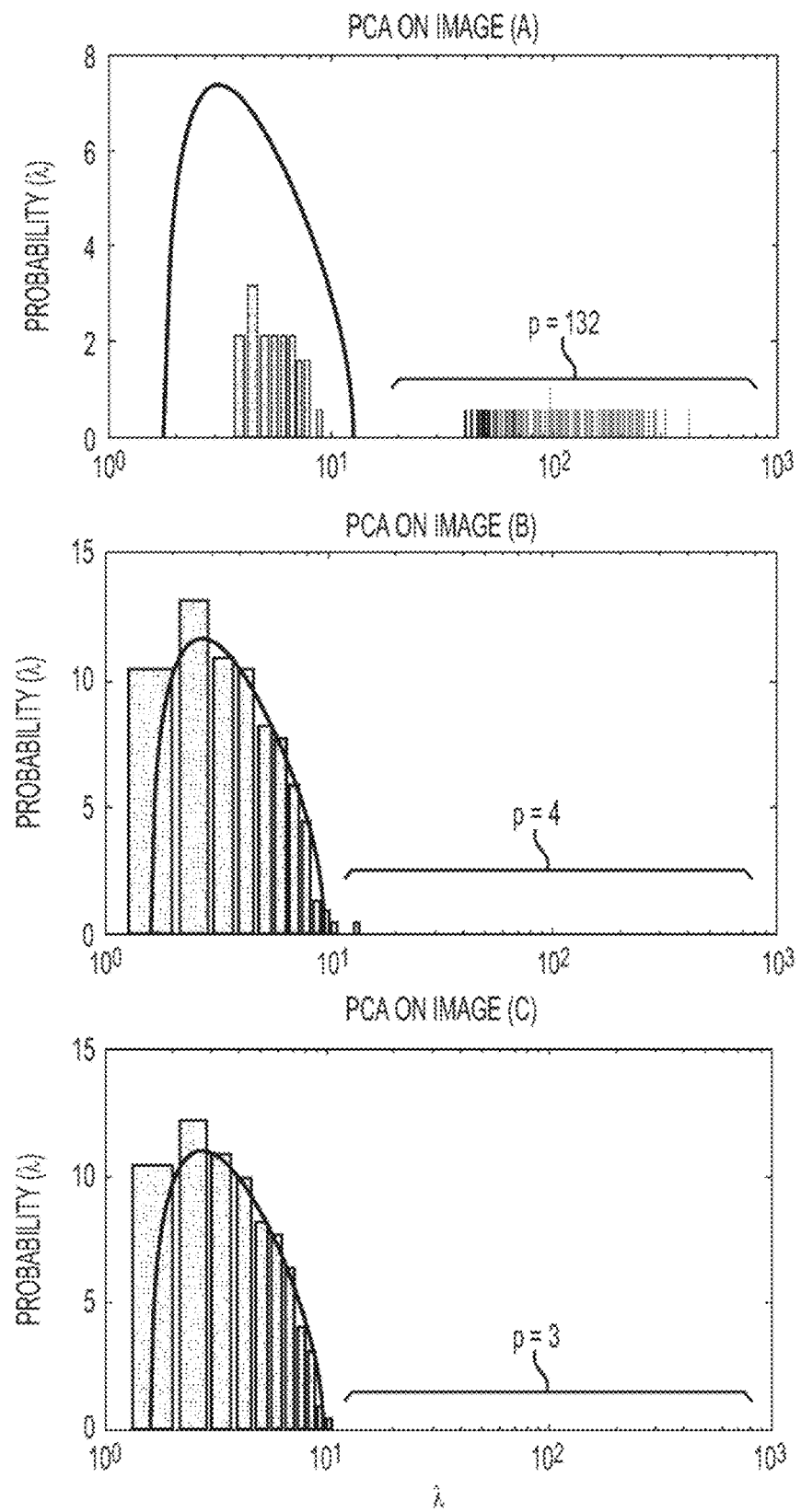
FIG. 11G shows a set of graphs of the exemplary PCA for FIGS. 11A-11C according to an exemplary embodiment of the present disclosure.

FIG. 11D shows a denoised coil image after nullifying the MP noise distribution in C; residual N/2 ghost due to imperfect ghost correction becomes visible after the denoising. FIGS. 11E and 11F show the full reconstruction following GRAPPA and POCS for the standard adaptive-combine (e.g., FIG. 11E) and coil-RMT (e.g., FIG. 11F) based on the phase-unwound images shown in FIG. 11C. FIG. 11G shows graphs of the exemplary PCA for FIGS. 11A-11C according to an exemplary embodiment of the present disclosure.

This approach preserves the noise statistics, as shown in FIG. 9A-9D; however, in the presence of asymmetric k-space undersampling such as partial Fourier, the merged lines can produce an image that can have a large phase shift in which the k=0 can be far from the center of undersampled k-space. This rapidly varying phase, in addition to the underlying phase, can add to the significant principal components, which can lower the efficiency of RMT denoising. This can benefit from unwinding of the phase prior to the RMT denoising, as described below.

Exemplary Phase Estimation and Unwinding

The relative coil phases can be estimated and unwound, which can otherwise contribute to the number of significant components P. (See e.g., images shown in FIG. 2B). Previous works estimate the phase either through regularization (see, e.g., Reference 44), or through k-space filters. (See, e.g., Reference 45). The aim of these previous approaches was to eliminate the Rician noise floor bias through a careful estimation of the phase that can push the relevant signal from the imaginary component into the real component, and thereby preserve Gaussian noise statistics for the real part. While these exemplary approaches can estimate the phase for each image individually, the exemplary system, method and computer-accessible medium can utilize the joint redundancy in the phase (e.g., shown in the images of FIGS. 10A-10D), over all coils and measurements.

An exemplary PCA procedure can be performed for each slice over a large 2-dimensional spatial patch, for example, $N_x$=15×15×1 (e.g., within a slice), including all coils and contrasts, forming the matrix X (e.g., with a different spatial extent), and estimate the phase Ø from a few of its largest principal components (such as, but not limited to, the largest principal component). The slices may not be included in the estimation of the phase, as the phase variations across slices can be far greater than the in-plane variation. For three-dimensional, non-echo-planar-imaging acquisitions, a differently selected patch can be used to estimate the phase, which can be a three-dimensional patch. After phase unwinding, there can be further reduction in the number of significant principal components, thereby increasing the efficiency of the denoising methodology (e.g., based on RMT) (see e.g., FIG. 2B). It can be beneficial that the spatial patch for the phase estimation can have little overlap with the spatial patch for the actual RMT denoising, to avoid introducing the correlations due to the noise in phase unwinding into the denoising step. Therefore, in some of the exemplary embodiments of the current disclosure, we used a large 2-dimensional patch within a slice, such as 15×15 or 7×7, for the phase estimation and unwinding, whereas we used a smaller 3×3×3 or 5×5×5 3-dimensional patch for the RMT denoising.

Exemplary RMT Denoising

RMT can be performed on a rank-3 (e.g., 3-dimensional tensor) object $\chi_{xcr}$ (e.g., or even higher rank/dimension, as described above, for example, containing information about different subjects and/or simulated data). This object's dimensions can contain information about voxels (or, equivalently, k-space point); MRI contrasts; and RF coils, where the noise can be made white and phases unwound, and which can subsequently be reshaped into a M×N object by choosing its largest dimension. If the noise is non-white, suitable extensions of the MP theory can be developed, where the eigenvalue thresholding can be performed based on the generalized pure-noise distribution that accounts the noise correlations (e.g., based on the noise covariance matrix Ψ). With a sufficiently large number $N_c$ of contrasts, the coils can be combined with the voxel patch, $N_c \times N_r N_x$, to create compact 3×3×3 or 5×5×5 patches, that exploit the spatial redundancy, such that the resulting P<<N, M. It can be feasible that with a sufficiently high number of coils, spatial redundancy can be maximized by reducing the spatial patch size to only a few, or even to a single voxel. Spatial patch may not necessarily be selected as a local patch, and other suitable methods of selecting voxels with similar biological or MRI properties (e.g., voxels belonging to atlas-based regions of interest, unifying voxels of a similar anatomical nature and function, and/or using nonlocal means methods based on similarity metrics between signals), can be utilized, to maximize the redundancy. Alternatively, with very few contrasts $N_c$~1, it can be beneficial to reshape the rank-3 (e.g., or higher-rank) measurement χ as, for example, $N_x \times N_c N_r$, (see e.g., FIG. 5A). One procedure can be to reshape a measurement tensor of any dimension (e.g., tensor rank) $\chi_{xcr...}$ into a 2-dimensional M×N matrix X such that its dimensions M and N may not be very different from each other, so that their ratio $$\gamma = \frac{M}{N} \sim 1,$$

for which the RMT application can be optimal.

Following RMT, the phase can be rewound and the k-space can be restored to its original format. For example, regridding, for example trapezoidal regridding, (see, e.g., Reference 46), can be performed immediately after, as it can have introduced noise-correlations along the frequency encoding direction. The missing k-space lines can be now filled with the procedure of choice (SENSE (see, e.g., Reference 41), GRAPPA (see, e.g., Reference 42), ESPIRiT (see, e.g., Reference 43), neural nets). (See, e.g., References 22 and 23). The coils can be combined via adaptive combine (see, e.g., Reference 36), where the local coil sensitivities $S_r(x)$ can be estimated as eigenvectors from the PCA denoising step using measurements from more than one contrast, resulting in very precise $S_r(x)$ maps to be employed in the optimal coil combination to produce the resulting images for each contrast.

Exemplary Experiments

The pulsed-gradient spin-echo ("PGSE") diffusion sequence was used to image water phantom and 2 brain datasets on a 3T Siemens PRISMA system with a 20 channel head/neck coil, of which 16 coil elements were enabled ($N_r$=16) during each scan and used for reconstruction. Parametric maps were derived via weighted linear least squares diffusion tensor/kurtosis imaging ("DTI"/"DKI") implemented in MATLAB. Brain ROIs were determined through registration of the JHU atlas.

Exemplary Water Phantom

A room-temperature water phantom (e.g., SNR=35 at b=0) (see e.g., MRI maps, the MRI signal as function of b-value, and the histogram of the estimated voxel-wise diffusion coefficients, shown in FIGS. 4A-4C, respectively, was imaged with 2.0 mm isotropic voxels, no parallel imaging, no partial Fourier, $T_R$=4200 ms, $T_E$=152 ms with 11b-shells (e.g., 6 directions each) up to b=4000 s/mm2 and 1 b=0. RMT was performed on the $N_c \times N_x N_r$ matrix, with $N_c$=67, $N_x$=5×3×3=45, $N_r$=16.

Exemplary Brain Slices at Different Resolutions

A 3-slice segment of a brain from a 31 y/o female volunteer was imaged at multiple isotropic resolutions [0.8, 0.9, 1.0, 1.5, 2.0] mm (e.g., SNR=[2.5, 3.1, 4.0, 7.9, 14.9] at b=0), no parallel imaging, partial Fourier 5/8 with POCS reconstruction, $T_R$=3000 ms, $T_E$=132 ms, with 8b-shells [0, 250, 500, 1000, 2000, 3000, 4000, 5000] s/mm$^2$ with [1, 6, 6, 12, 20, 30, 30, 40] directions for each shell, respectively. The acquisition time for each resolution was 7 minutes. Images were registered via affine+bspline transforms via the ELASTIX toolbox. RMT was performed on the $N_c \times N_x N_r$ matrix, with $N_c$=145, $N_x$=5×3×3=45, $N_r$=16.

Exemplary Full-Brain at 0.8 mm Isotropic Resolution

A full brain of a 34 y/o male volunteer (e.g., SNR=13-15 at b=0) was imaged with 0.8 mm isotropic resolution, parallel imaging R=2 reconstructed with GRAPPA, partial Fourier 5/8 reconstructed with POCS, $T_R$=3100 ms, $T_E$=75 ms, 10b=0, 20b=1000 s/mm$^2$, 40b=2000 s/mm$^2$. RMT denoising was performed on the $N_c \times N_x N_r$ matrix, with $N_c$=70, $N_x$=5×3×3=45, $N_r$=16. Due to computer memory constraints, this dataset was acquired with 5 segments of 26 slices that were fused in post-processing, each segment was acquired in 4:36 or 23 minutes in total. Diffusion images were processed via the DESIGNER pipeline (see, e.g., Reference 40), and ODFs and probabilistic tractography both was generated and visualized using mrtrix3 open-source library.

Figure 12:
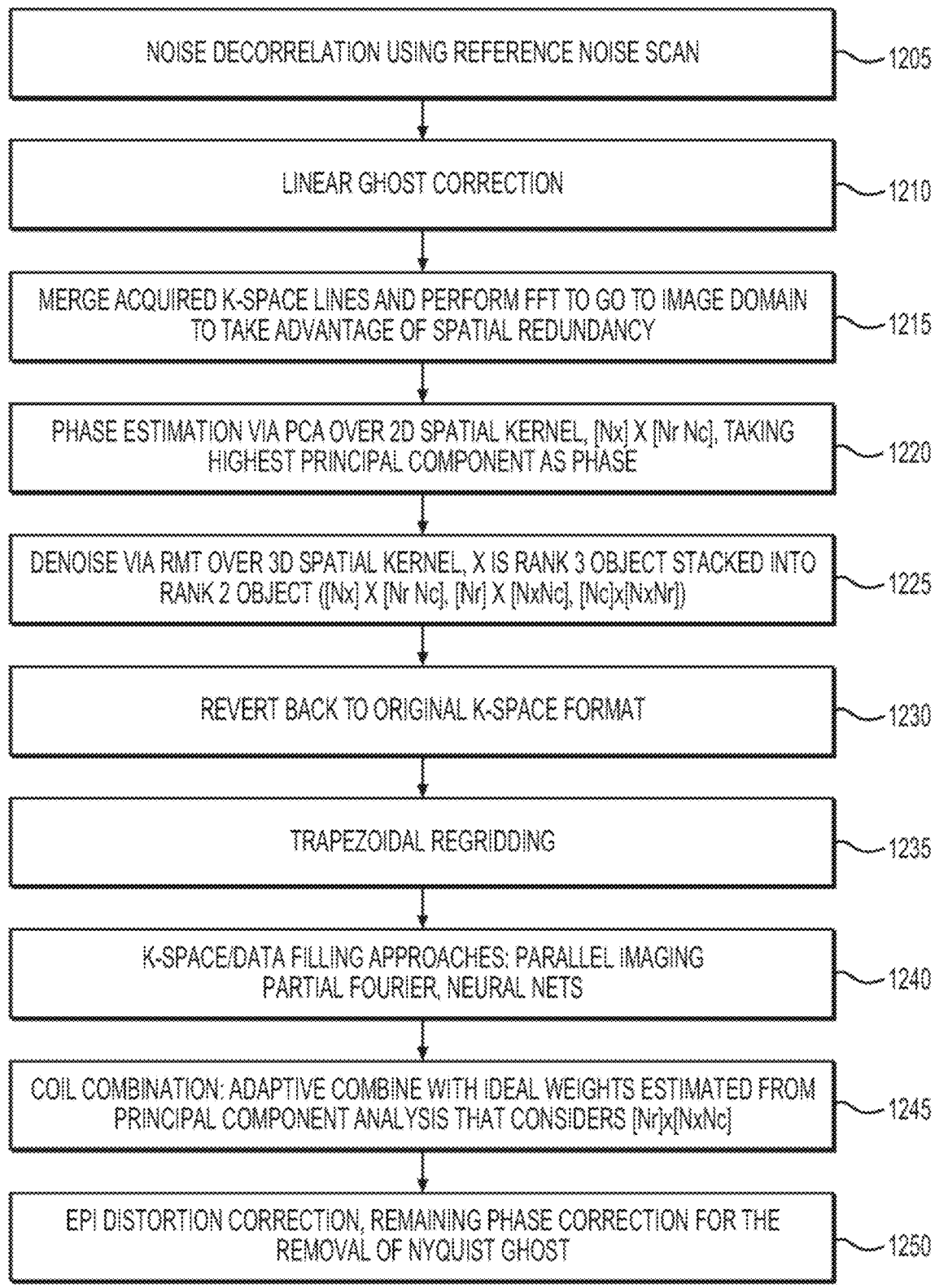
FIG. 12 shows an exemplary flow diagram of a method for generating a denoised magnetic resonance image of a portion of a patient according to an exemplary embodiment of the present disclosure.

FIG. 12 shows an exemplary flow diagram of a method 1200 for generating a denoised magnetic resonance (MR) image of a portion of a patient according to an exemplary embodiment of the present disclosure. For example, procedure 1205 can include performing coil noise decorrelation, using either a noise only reference scan or a noise estimation approach if no reference scan is available. Nyquist ghost correction can occur for echo planar imaging ("EPI") trajectories, when there can be a mismatch between the alignment of odd and even k-space lines. Linear ghost correction $\Phi(x)=\phi_1 x+\phi_0$, can be for example performed prior to denoising, as this correction may not impact noise statistics, but can increase spatial redundancy by suppressing the Nyquist ghost in procedure 1210. Alternatively, or in addition, ghost correction procedures can be used for, for example, non-EPI acquisitions. At procedure 1215, merging of k-space lines can be performed to preserve white noise statistics by performing subsequent RMT methodology on only the acquired k-space lines, and utilizing spatial redundancy by applying RMT in the image domain. At procedure 1220, the relative coil phases can be estimated and unwound by utilizing the joint redundancy in the phase over all coils and measurements, where, for example, the phase of the highest (e.g., or a few highest) principal component(s) can be estimated and unwound.

At procedure 1225, a 2-dimensional matrix X can be built/generated from a rank-3 or higher-rank-tensor measurement χ by reshaping (e.g., stacking) its dimensions, and applying the thresholding (e.g., soft or hard thresholding) procedure to the eigenvalues, or more generally, identifying the pure-noise components in χ based on the statistics of the pure-noise measurement. At procedure 1230, the denoising can be performed in the image-space, such that the data can be transformed back into MRI k-space, which can include the phase re-winding (e.g., adding the complex phase that was estimated and unwound at procedure 1220). Optionally, regridding can be performed at 1235 (e.g., trapezoidal).

The denoised data can be reconstructed at procedure 1240 using any suitable reconstruction procedure. Such reconstruction can also proceed right after the denoising procedure 1225, by, for example, training a neural network to perform reconstruction from the basis in which the RMT denoising is performed, such that procedures 1230 and 1235 can be skipped. The data reconstruction can include coil combination, such as, but not limited to, optimal/adaptive coil combination, at procedure 1245. In this procedure, coil sensitivities can be used that can be estimated from the RMT denoising procedure 1225. At procedure 1250, artifact correction can be performed (e.g., due to EPI distortions, residual ghosting, etc.). Procedures 1230 and beyond can be substituted by a suitable reconstruction procedure (e.g., a neural network-based reconstruction) trained on a given undersampling pattern. As long as this reconstruction can be performed after the denoising procedure, the resulting image quality can be improved.

Figure 13:
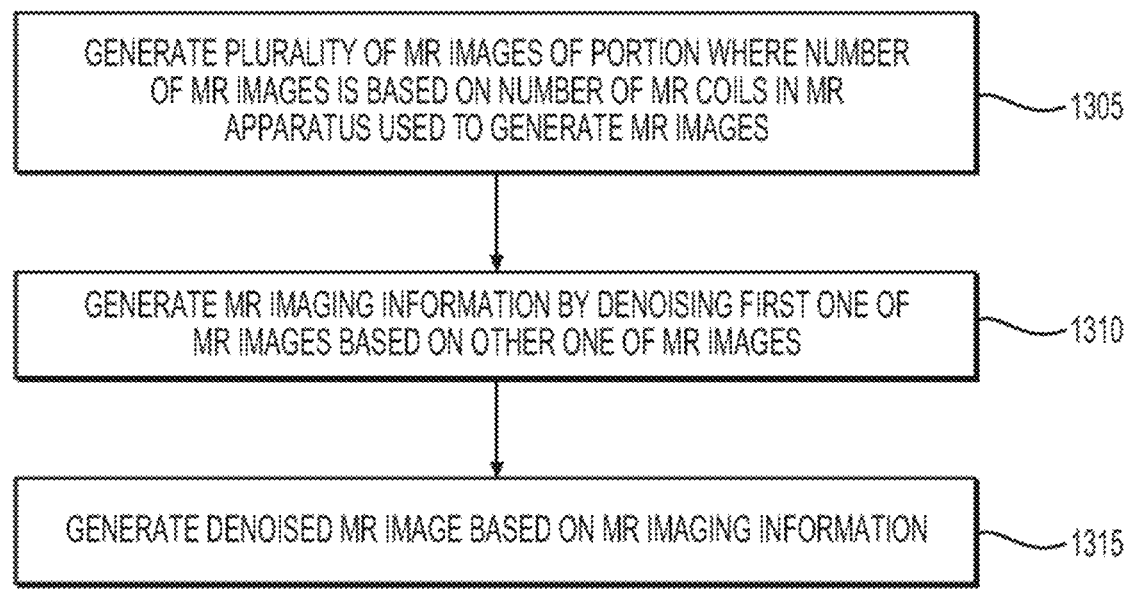
FIG. 13 shows a further exemplary flow diagram of a method for generating a denoised magnetic resonance image of a portion of a patient according to an exemplary embodiment of the present disclosure.

FIG. 13 shows an exemplary flow diagram of a method 1300 for generating a denoised magnetic resonance (MR) image of a portion of a patient according to an exemplary embodiment of the present disclosure. For example, at procedure 1305, a plurality of MR images of a portion of a patient can be generated where the number of the MR images can be based on the number of MR coils in the MR apparatus used to generate the MR images. At procedure 1310, MR imaging information can be generated by denoising a first one of the MR images based on another one of the MR images. At procedure 1315, a denoised MR image can be generated based on the MR imaging information.

Figure 14:
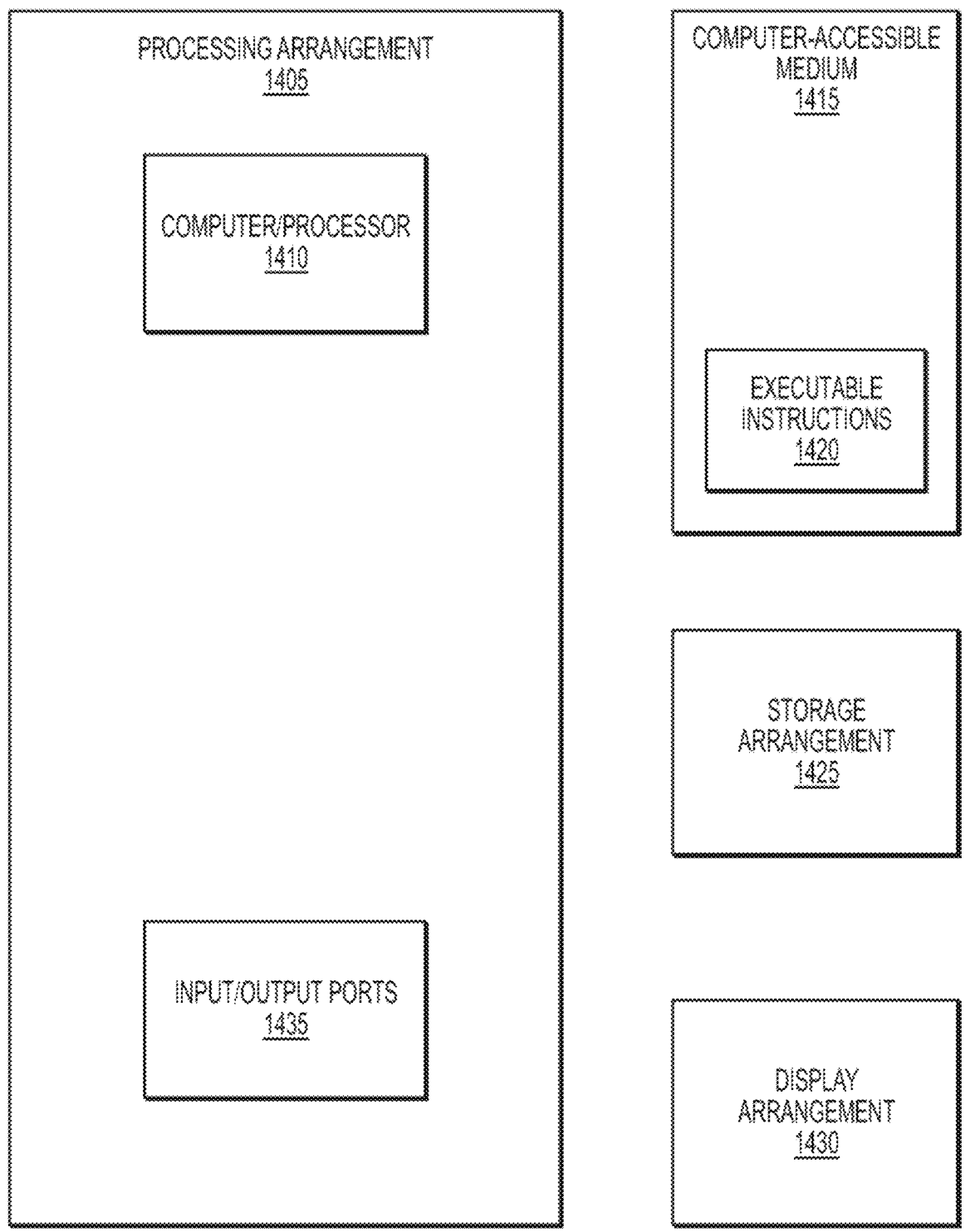
FIG. 14 is an illustration of an exemplary block diagram of an exemplary system in accordance with certain exemplary embodiments of the present disclosure.

FIG. 14 shows a block diagram of an exemplary embodiment of a system according to the present disclosure. For example, exemplary procedures in accordance with the present disclosure described herein can be performed by a processing arrangement and/or a computing arrangement (e.g., computer hardware arrangement) 1405. Such processing/computing arrangement 1405 can be, for example entirely or a part of, or include, but not limited to, a computer/processor 1410 that can include, for example one or more microprocessors, and use instructions stored on a computer-accessible medium (e.g., RAM, ROM, hard drive, or other storage device).

As shown in FIG. 14, for example a computer-accessible medium 1415 (e.g., as described herein above, a storage device such as a hard disk, floppy disk, memory stick, CD-ROM, RAM, ROM, etc., or a collection thereof) can be provided (e.g., in communication with the processing arrangement 1405). The computer-accessible medium 1415 can contain executable instructions 1420 thereon. In addition, or alternatively, a storage arrangement 1425 can be provided separately from the computer-accessible medium 1415, which can provide the instructions to the processing arrangement 1405 so as to configure the processing arrangement to execute certain exemplary procedures, processes, and methods, as described herein above, for example.

Further, the exemplary processing arrangement 1405 can be provided with or include an input/output ports 1435, which can include, for example a wired network, a wireless network, the internet, an intranet, a data collection probe, a sensor, etc. As shown in FIG. 14, the exemplary processing arrangement 1405 can be in communication with an exemplary display arrangement 1430, which, according to certain exemplary embodiments of the present disclosure, can be a touch-screen configured for inputting information to the processing arrangement in addition to outputting information from the processing arrangement, for example. Further, the exemplary display arrangement 1430 and/or a storage arrangement 1425 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference, in their entireties:
[1] T. E. Conturo, N. F. Lori, T. S. Cull, E. Akbudak, A. Z. Snyder, J. S. Shimony, R. C. McKinstry, H. Burton, and M. E. Raichle, "Tracking neuronal fiber pathways in the living human brain," Pro¬ceedings of the National Academy of Sciences 96, 10422-10427 (1999), arXiv:NIHMS 150003.
[2] S Mori, B J Crain, V P Chacko, and P C van Zijl, "Three-dimensional tracking of axonal projections in the brain by magnetic resonance imaging." Ann Neurol 45, 265-269 (1999).
[3] Peter J Basser, Sinisa Pajevic, Carlo Pierpaoli, Jeffrey Duda, and Akram Aldroubi, "In Vivo Fiber Tractography," Magnetic Resonance in Medicine 44, 625-632 (2000).
[4] Saad Jbabdi, Stamatios N Sotiropoulos, Suzanne N Haber, David C Van Essen, Timothy E Behrens, David C Van Essen, and Timothy E Behrens, "Measuring macroscopic brain connections in vivo," Nature Neuroscience 18, 1546-1555 (2015).
[5] Klaus H. Maier-Hein, Peter F. Neher, Jean Christophe Houde, Marc Alexandre Côte, Eleftherios Gary-fallidis, Jidan Zhong, Maxime Chamberland, Fang Cheng Yeh, Ying Chia Lin, Qing Ji, Wilburn E. Reddick, John O. Glass, David Qixiang Chen, Yuanjing Feng, Chengfeng Gao, Ye Wu, Jieyan Ma, H. Renjie, Qiang Li, Carl Fredrik Westin, Samuel Deslauriers-Gauthier, J. Omar Ocegueda Gonza´lez, Michael Paquette, Samuel St-Jean, Gabriel Girard, Franc,ois Rheault, Jasmeen Sidhu, Chantal M.W. Tax, Fenghua Guo, Hamed Y. Mesri, Szabolcs Da´vid, Martijn Froeling, Anneriet M. Heemskerk, Alexander Leemans, Arnaud Bore, Basile Pinsard, Christophe Bedetti, Matthieu Desrosiers, Simona Brambati, Julien Doyon, Alessia Sarica, Roberta Vasta, Antonio Cerasa, Aldo Quattrone, Jason Yeat-man, Ali R. Khan, Wes Hodges, Simon Alexander, David Romascano, Muhamed Barakovic, Anna Auri´a, Oscar Esteban, Alia Lemkaddem, Jean Philippe Thiran, H. Ertan Cetingul, Benjamin L. Odry, Boris Mailhe, Mariappan S. Nadar, Fabrizio Pizzagalli, Gautam Prasad, Julio E. Villalon-Reina, Justin Galvis, Paul M. Thompson, Francisco De Santiago Requejo, Pedro Luque Laguna, Luis Miguel Lac-erda, Rachel Barrett, Flavio Dell'Acqua, Marco Catani, Laurent Petit, Emmanuel Caruyer, Alessandro Daducci, Tim B. Dyrby, Tim Holland-Letz, Claus C. Hilgetag, Bram Stieltjes, and Maxime De-scoteaux, "The challenge of mapping the human connectome based on diffusion tractography," Nature Communications 8 (2017), 10.1038/s41467-017-01285-x.
[6] S Ogawa, T M Lee, A R Kay, and D W Tank, "Brain magnetic resonance imaging with contrast dependent on blood oxygenation." Proceedings of the National Academy of Sciences of the United States of America 87, 9868-9872 (1990).
[7] J W Belliveau, D N Kennedy, R C McKinstry, B R Buchbinder, R M Weisskoff, M S Cohen, J M Vevea, T J Brady, and B R Rosen, "Functional mapping of the human visual cortex by magnetic resonance imaging." Science (New York, N.Y.) 254, 716-9 (1991).
[8] Seiji Ogawa, David W Tank, Ravi Menon, Jutta M Ellermann, Seong-Gi Kim, Hellmut Merkle, and Kamil Ugurbil¯ Shin, Michael Lustig, and Ana C Arias, "Screen-printed flexible MRI receive coils," Nature Communications 7, 10839 (2016).
[9] M E Moseley, Y Cohen, J Mintorovitch, L Chileuitt, H Shimizu, J Kucharczyk, M F Wendland, and P R Weinstein, "Early detection of regional cerebral-ischemia in cats—comparison of diffusion-weighted and T2-weighted MRI and spectroscopy," Magnetic Resonance In Medicine 14, 330-346 (1990).
[10] P C Lauterbur, "Image formation by induced local interactions. Examples employing nuclear magnetic resonance," Nature (London, United Kingdom) 242, 190-191 (1973).
[11] P. B. Roemer, W. A. Edelstein, C. E. Hayes, S. P. Souza, and O. M. Mueller, "The NMR phased array," Magnetic Resonance in Medicine 16, 192-225 (1990).
[12] Florian Wiesinger, Peter Boesiger, and Klaas P. Pruessmann, "Electrodynamics and ultimate SNR in parallel MR imaging," Magnetic Resonance in Medicine 52, 376-390 (2004).
[13] Riccardo Lattanzi and Daniel K. Sodickson, "Ideal current patterns yielding optimal signal-to-noise ratio and specific absorption rate in magnetic resonance imaging: Computational methods and physi¬cal insights," Magnetic Resonance in Medicine 68, 286-304 (2012).

[14] Joseph R Corea, Anita M Flynn, Balthazar Lechêne, Greig Scott, Galen D Reed, Peter J Shin, Michael Lustig, and Ana C Arias, "Screen-printed flexible MRI receive coils," Nature Communications 7, 10839 (2016).

[15] HáKon Gudbjartsson and Samuel Patz, "The rician distribution of noisy MRI data," Magnetic Resonance in Medicine 34, 910-914 (1995).

[16] Eugene P. Wigner, "On the Distribution of the Roots of Certain Symmetric Matrices," Annals of Mathematics 67, 325-327 (1958).

[17] Freeman J. Dyson, "A BrownianMotion Model for the Eigenvalues of a Random Matrix," Journal of Mathematical Physics 3, 1191-1198 (1962).

[18] V A Marchenko and L A Pastur, "Distribution of Eigenvalues for Some Sets of Random Matrices," Mathematics of the USSR-Sbornik 1, 457-483 (1967).

[19] Jinho Baik, Gérard Ben Arous, and Sandrine Péché, "Phase transition of the largest eigenvalue for nonnull complex sample covariance matrices," The Annals of Probability 33, 1643-1697 (2005).

[20] Iain M. Johnstone, "High dimensional statistical inference and random matrices," Proceedings of the International Congress of Mathematicians, Madrid, Aug. 22-30, 2006, 307-333 (2007), arXiv:0611589.

[21] Dan Ma, Vikas Gulani, Nicole Seiberlich, Kecheng Liu, Jeffrey L Sunshine, Jeffrey L Duerk, and Mark A Griswold, "Magnetic resonance fingerprinting," Nature 495, 187-192 (2013).

[22] Kerstin Hammernik, Teresa Klatzer, Erich Kobler, Michael P. Recht, Daniel K. Sodickson, Thomas Pock, and Florian Knoll, "Learning a variational network for reconstruction of accelerated mri data," Magnetic Resonance in Medicine 79, 3055-3071 (2018).

[23] Bo Zhu, Jeremiah Z Liu, Stephen F Cauley, Bruce R Rosen, and Matthew S Rosen, "Image reconstruction by domain-transform manifold learning," Nature 555, 487-492 (2018).

[24] Ogan Ocali and Ergin Atalar, "Ultimate intrinsic signal-to-noise ratio in MRI," Magnetic Resonance in Medicine 39, 462-473 (1998).

[25] Qiuyun Fan, Thomas Witzel, Aapo Nummenmaa, Koene R A Van Dijk, John D Van Horn, Michelle K Drews, Leah H Somerville, Margaret A Sheridan, Rosario M Santillana, Jenna Snyder, Trey Hedden, Emily E Shaw, Marisa O Hollinshead, Ville Renvall, Roberta Zanzonico, Boris Keil, Stephen Cauley, Jonathan R Polimeni, Dylan Tisdall, Randy L Buckner, Van J Wedeen, Lawrence L Wald, Arthur W Toga, and Bruce R Rosen, "MGH-USC Human Connectome Project datasets with ultra-high b-value diffusion MRI," NeuroImage 124, 1108-1114 (2016).

[26] Daniel K. Sodickson, Riccardo Lattanzi, Manushka Vaidya, Gang Chen, Dmitry S. Novikov, Christopher M. Collins, and Graham C. Wiggins, "The Optimality Principle for MR signal excitation and reception: New physical insights into ideal radiofrequency coil design," arXiv e-prints, arXiv:1808.02087 (2018), arXiv:1808.02087 [physics.ins-det].

[27] Thomas F. Budinger, Mark D. Bird, Lucio Frydman, Joanna R. Long, Thomas H. Mareci, William D. Rooney, Bruce Rosen, John F. Schenck, Victor D. Schepkin, A. Dean Sherry, Daniel K. Sodickson, Charles S. Springer, Keith R. Thulborn, Kamil Uǧurbil, and Lawrence L. Wald, "Toward 20 t magnetic resonance for human brain studies: opportunities for discovery and neuroscience rationale," Magnetic Resonance Materials in Physics, Biology and Medicine 29, 617-639 (2016).

[28] Oliver Kraff and Harald H. Quick, "7t: Physics, safety, and potential clinical applications," Journal of Magnetic Resonance Imaging 46, 1573-1589 (2017), https://onlinelibrary.wiley.com/doi/pdf/10.1002/jmri.25723.

[29] Thomas Budinger, "Nuclear magnetic resonance (nmr) in vivo studies: Known thresholds for health effects," Journal of computer assisted tomography 5, 800-11 (1982).

[30] Allahyar Kangarlu and Pierre-Marie L Robitaille, "Biological effects and health implications in magnetic resonance imaging," Concepts in Magnetic Resonance: An Educational Journal 12, 321-359 (2000).

[31] Derek K Jones, Diffusion MRI: Theory, Methods, and Applications (Oxford University Press, New York, 2010).

[32] C. W. J. Beenakker, "Random-matrix theory of quantum transport," Rev. Mod. Phys. 69, 731-808 (1997).

[33] Jelle Veraart, Dmitry S. Novikov, Daan Christiaens, Benjamin Ades-Aron, Jan Sijbers, and Els Fieremans, "Denoising of diffusion MRI using random matrix theory," NeuroImage 142, 394-406 (2016).

[34] Jelle Veraart, Els Fieremans, and Dmitry S Novikov, "Diffusion MRI noise mapping using random matrix theory," Magnetic resonance in medicine 76, 1582-1593 (2016).

[35] M. Gavish and D. L. Donoho, "Optimal shrinkage of singular values," IEEE Transactions on Information Theory 63, 2137-2152 (2017).

[36] David O. Walsh, Arthur F. Gmitro, and Michael W. Marcellin, "Adaptive reconstruction of phased array MR imagery," Magnetic Resonance in Medicine 43, 682-690 (2000).

[37] D S Novikov, E Fieremans, S N Jespersen, and V G Kiselev, "Quantifying brain microstructure with diffusion MRI: Theory and parameter estimation," NMR in Biomedicine 32, e3998 (2019).

[38] C B Ahn and Zang Cho, "A new phase correction method in nmr imaging based on autocorrelation and histogram analysis," IEEE transactions on medical imaging 6, 32-6 (1987).

[39] Victor B Xie, Mengye Lyu, Yilong Liu, Yanqiu Feng, and Ed Wu, "Robust epi nyquist ghost removal by incorporating phase error correction with sensitivity encoding (pec-sense)," Magnetic resonance in medicine 79 (2017), 10.1002/mrm.26710.

[40] Benjamin Ades-Aron, Jelle Veraart, Peter Kochunov, Stephen McGuire, Paul Sherman, Elias Kellner, Dmitry S. Novikov, and Els Fieremans, "Evaluation of the accuracy and precision of the diffusion parameter estimation with gibbs and noise removal pipeline," NeuroImage 183, 532-543 (2018).

[41] Klaas P Pruessmann, "Encoding and reconstruction in parallel MRI," NMR in Biomedicine 19, 288-299 (2006).

[42] Mark A. Griswold, Peter M. Jakob, Robin M. Heidemann, Mathias Nittka, Vladimir Jellus, Jianmin Wang, Berthold Kiefer, and Axel Haase, "Generalized Autocalibrating Partially Parallel Acquisitions (GRAPPA)," Magnetic Resonance in Medicine 47, 1202-1210 (2002).

[43] Martin Uecker, Peng Lai, Mark J Murphy, Patrick Virtue, Michael Elad, John Pauly, Shreyas S Vasanawala, and Michael Lustig, "Espiritâan eigenvalue approach to autocalibrating parallel mri: where sense meets grappa," Magnetic resonance in medicine: official journal of the Society of Magnetic Resonance in Medicine/Society of Magnetic Resonance in Medicine 71 (2014), 10.1002/mrm.24751.

[44] Cornelius Eichner, Stephen F Cauley, Julien Cohen-Adad, Harald Mäller, Robert Turner, Kawin Setsompop, and Lawrence Wald, "Real diffusion-weighted mri enabling true signal averaging and in-creased diffusion contrast," NeuroImage 122 (2015), 10.1016/j.neuroimage.2015.07.074.
[45] Tim Sprenger, Jonathan Sperl, Brice Fernandez, Axel Haase, and Marion Menzel, "Real valued diffusion-weighted imaging using decorrelated phase filtering," Magnetic Resonance in Medicine 77, n/a-n/a (2016).
[46] MATT A. BERNSTEIN, KEVIN F. KING, and XIAO-HONG JOE ZHOU, "Chapter 16—echo train pulse sequences," in Handbook of MRI Pulse Sequences, edited by MATT A. BERNSTEIN, KEVIN F. KING, and XIAO-HONG JOE ZHOU (Academic Press, Burlington, 2004) pp. 702-801.
[47] N. Martini, M. F. Santarelli, G. Giovannetti, M. Milanesi, D. De Marchi, V. Positano, and L. Lan-dini, "Noise correlations and snr in phased-array mrs," NMR in Biomedicine 23, 66-73 (2010), https://onlinelibrary.wiley.com/doi/pdf/10.1002/nbm.1429.
[48] Katherine L. Wright, Jesse I. Hamilton, Mark A. Griswold, Vikas Gulani, and Nicole Seiberlich, "Non-cartesian parallel imaging reconstruction," Journal of Magnetic Resonance Imaging 40, 1022-1040 (2014), https://onlinelibrary.wiley.com/doi/pdf/10.1002/jmri.24521.
[49] G. McGibney, M. R. Smith, S. T. Nichols, and A. Crawley, "Quantitative evaluation of several partial fourier reconstruction algorithms used in mri," Magnetic Resonance in Medicine 30, 51-59 (1993), https://onlinelibrary.wiley.com/doi/pdf/10.1002/mrm.1910300109.
[50] Paul Margosian, F Schmitt, and Purdy D E, "Faster mr imaging: Imaging with half the data," Health Care Instrumentation 1, 195-197 (1986).
[51] Laurent Laloux, Pierre Cizeau, Jean-Philippe Bouchaud, and Marc Potters, "Noise Dressing of Finan-cial Correlation Matrices," Physical Review Letters 83, 1467-1470 (1999), vv:9810255 [cond-mat].
[52] S Jbabdi, M W Woolrich, J L R Andersson, and T E J Behrens, "A Bayesian framework for global tractography," NeuroImage 37, 116-129 (2007).
[53] Cheng Guan Koay, Evren O¨zarslan, and Peter J. Basser, "A signal transformational framework for breaking the noise floor and its applications in MRI," Journal of Magnetic Resonance 197, 108-119 (2009).
[54] Emilie T McKinnon, Jens H Jensen, G Russell Glenn, and Joseph A Helpern, "Dependence on b-value of the direction-averaged diffusion-weighted imaging signal in brain," Magnetic Resonance Imaging 36, 121-127 (2016).
[55] Jelle Veraart, Els Fieremans, and Dmitry S Novikov, "NeuroImage On the scaling behavior of water diffusion in human brain white matter," NeuroImage 185, 379-387 (2019).

What is claimed is:

1. A non-transitory computer-accessible medium having stored thereon computer-executable instructions for generating at least one denoised magnetic resonance (MR) image of at least one portion of at least one patient, wherein, when a computer arrangement executes the instructions, the computer arrangement is configured to perform procedures comprising:
generating a plurality of MR images of the at least one portion, wherein:
a number of the MR images is based on a number of MR coils in a MR apparatus used to generate the MR images;
each of at least two of the MR images is associated with a respective distinct information item indicating a respective distinct one of the MR coils; and
each of the respective distinct ones of the MR coils is associated with one of the respective distinct information items of the at least two of the MR images;
generating MR imaging information by denoising a first one of the MR images based on at least one other of the MR images and the information items associated with each of the at least two of the MR images, wherein the first one of the MR images and the at least one other of the MR images share information; and
generating the at least one denoised MR image based on the MR imaging information, wherein the at least one denoised MR image is generated using a principal component analysis procedure.

2. The computer-accessible medium of claim 1, wherein the number of the MR coils is a subset of a total number of the MR coils in the MR apparatus.

3. The computer-accessible medium of claim 1, wherein the number of the MR coils is a total number of the MR coils in the MR apparatus.

4. The computer-accessible medium of claim 1, wherein the computer arrangement is configured to generate the MR information by denoising each of the MR images based on at least one of (i) the at least one other of the MR images, (ii) every one of the MR images.

5. The computer-accessible medium of claim 1, wherein the number of the MR images is further based on a real part of a signal and an imaginary part of a signal produced using the MR coils.

6. The computer-accessible medium of claim 1, wherein the computer arrangement is configured to generate the MR imaging information using a reconstruction procedure.

7. The computer-accessible medium of claim 6, wherein the reconstruction procedure is a denoising procedure.

8. The computer-accessible medium of claim 7, wherein the denoising procedure is a random matrix theory procedure.

9. The computer-accessible medium of claim 1, wherein the computer arrangement is configured to generate the at least one denoised MR image using a reconstruction procedure.

10. The computer-accessible medium of claim 9, wherein the reconstruction procedure is at least one of (i) an adaptive-combine reconstruction procedure, or (ii) a denoising procedure.

11. The computer-accessible medium of claim 1, wherein the number of the MRI images is based on a MR imaging procedure being performed using the MR apparatus.

12. The computer-accessible medium of claim 11, wherein the MR imaging procedure is at least one of (i) diffusion imaging procedure, (ii) perfusion MR imaging, (iii) functional MR imaging, (iv) MR imaging fingerprinting, (iv) a multi-contrast imaging procedure, or (v) a multi-modal imaging procedure.

13. The computer-accessible medium of claim 1, wherein the computer arrangement is configured to generate the MR imaging information by decorrelating noise using a plurality of MR coil combinations.

14. The computer-accessible medium of claim 1, wherein the computer arrangement is configured to generate the MR imaging information using a Nyquist ghost correction procedure.

15. The computer-accessible medium of claim 14, wherein the Nyquist ghost correction procedure is based on odd scan lines and even scan lines.

16. The computer-accessible medium of claim 1, wherein the computer arrangement is further configured to generate the MR imaging information based on an estimated coil sensitivity for each of the MR coils.

17. The computer-accessible medium of claim 1, wherein the computer arrangement is configured to generate the MR imaging information using a phase estimation procedure.

18. The computer-accessible medium of claim 17, wherein the phase estimation procedure is configured to estimate a phase using one or a few principal components from a matrix constructed based on a sliding window.

19. The computer-accessible medium of claim 1, wherein the computer arrangement is configured to generate the MR imaging information using a phase unwinding procedure, and wherein the phase unwinding procedure includes a joint redundancy in at least one phase and at least one measurement over all the MR coils.

20. The computer-accessible medium of claim 1, wherein the phase unwinding procedure is performed to improve a performance of random matrix theory ("RMT") denoising or reconstruction for generating the at least one denoised MR image.

21. The computer-accessible medium of claim 1, wherein the first one of the MR images and the at least one other of the MR images were captured at different points in time and the plurality of MR images are provided in the same segment of k-space.

22. A method for generating at least one denoised magnetic resonance (MR) image of at least one portion of at least one patient, comprising:
generating a plurality of MR images of the at least one portion, wherein:
a number of the MR images is based on a number of MR coils in a MR apparatus used to generate the MR images;
each of at least two of the MR images is associated with a respective distinct information item indicating a respective distinct one of the MR coils; and
each of the respective distinct ones of the MR coils is associated with one of the respective distinct information items of the at least two of the MR images;
generating MR imaging information by denoising a first one of the MR images based on at least one other of the MR images and the information items associated with each of the at least two of the MR images, wherein the first one of the MR images and the at least one other of the MR images share information; and
using a computer hardware arrangement, generating the at least one denoised MR image based on the MR imaging information, wherein the at least one denoised MR image is generated using a principal component analysis procedure.

23. A system for generating at least one denoised magnetic resonance (MR) image of at least one portion of at least one patient, comprising:
a computer hardware arrangement configured to:
generate a plurality of MR images of the at least one portion, wherein:
a number of the MR images is based on a number of MR coils in a MR apparatus used to generate the MR images;
each of at least two of the MR images is associated with a respective distinct information item indicating a respective distinct one of the MR coils; and
each of the respective distinct ones of the MR coils is associated with one of the respective distinct information items of the at least two of the MR images;
generate MR imaging information by denoising a first one of the MR images based on at least one other of the MR images and the information items associated with each of the at least two of the MR images, wherein the first one of the MR images and the at least one other of the MR images share information; and
generate the at least one denoised MR image based on the MR imaging information, wherein the at least one denoised MR image is generated using a principal component analysis procedure.

* * * * *